US008158441B2

(12) United States Patent
Cecillon et al.

(10) Patent No.: US 8,158,441 B2
(45) Date of Patent: *Apr. 17, 2012

(54) METHOD FOR DETECTING AGGREGATE-FORMING CIRCULATING PROTEIN FORMS USING AN AGENT FOR AGGREGATING SAID FORMS AND AN AGENT FOR CAPTURING FORMED AGGREGATES

(75) Inventors: Sébastien Cecillon, Lyons (FR); Anthony William Coleman, Caluire (FR); Anne Eveno-Nobile, Dolomieu (FR); Hervé Perron, Saint Genis les Ollieres (FR); Marc Rodrigue, Grezieu la Varenne (FR)

(73) Assignees: Biomerieux S.A., Marcy l'Etoile (FR); Centre National de la Recherche Scientifique, Paris (FR); Universite Claude Bernard Lyon 1, Villeurbanne (FR)

( * ) Notice: Subject to any disclaimer, the term of this patent is extended or adjusted under 35 U.S.C. 154(b) by 892 days.

This patent is subject to a terminal disclaimer.

(21) Appl. No.: 11/988,402

(22) PCT Filed: Jul. 7, 2006

(86) PCT No.: PCT/FR2006/001641
§ 371 (c)(1),
(2), (4) Date: Jan. 7, 2008

(87) PCT Pub. No.: WO2007/010110
PCT Pub. Date: Jan. 25, 2007

(65) Prior Publication Data
US 2010/0062540 A1 Mar. 11, 2010

(30) Foreign Application Priority Data
Jul. 21, 2005 (FR) ...................... 05 07757

(51) Int. Cl.
*G01N 33/53* (2006.01)
*G01N 33/68* (2006.01)
(52) U.S. Cl. .............. 436/501; 435/7.1; 435/81; 436/86
(58) Field of Classification Search ........................ None
See application file for complete search history.

(56) References Cited

U.S. PATENT DOCUMENTS

| 6,054,114 | A | 4/2000 | Lansbury et al. | |
|---|---|---|---|---|
| 6,137,014 | A | 10/2000 | Van Kruchten | |
| 6,365,414 | B1 | 4/2002 | Tanzi et al. | |
| 6,887,676 | B1 | 5/2005 | Collinge et al. | |
| 7,217,530 | B2 * | 5/2007 | Moussa et al. ............... | 435/7.1 |
| 7,566,530 | B2 * | 7/2009 | Benscik-Reynier et al. ..... | 435/5 |
| 7,695,918 | B2 * | 4/2010 | Moussa et al. ............... | 435/7.1 |
| 2002/0137114 | A1 | 9/2002 | Voelkel et al. | |
| 2004/0096902 | A1 | 5/2004 | Kiesewetter et al. | |
| 2005/0221404 | A1 | 10/2005 | Lane et al. | |
| 2006/0014215 | A1 | 1/2006 | Moussa et al. | |
| 2006/0019311 | A1 | 1/2006 | Moussa et al. | |

FOREIGN PATENT DOCUMENTS

| EP | 0 713 095 A2 | 5/1996 |
|---|---|---|
| FR | 2 849 204 | 6/2004 |
| FR | 2 865 280 A1 | 7/2005 |
| WO | WO 00/62068 A1 | 10/2000 |
| WO | WO 02/065133 A2 | 8/2002 |
| WO | WO 02/086511 A2 | 10/2002 |
| WO | WO 03/073106 A2 | 9/2003 |
| WO | WO 2004/059321 A1 | 7/2004 |
| WO | WO 2004/059322 A1 | 7/2004 |
| WO | WO 2005/026740 A1 | 3/2005 |

OTHER PUBLICATIONS

Anonymous, "Amyloid," Wikipedia, XP-002375713, http://web.archive.org/web/20050319085527/http://en.wikipedia.org/wiki/Amyloid, Mar. 17, 2003.
Paudel, H. K. et al., "Herapin-Induced Conformational Change in Microtube-Associated Protein Tau as Detected by Chemical Cross-Linking and Phosphopeptide Mapping*," The Journal of Biological Chemistry, vol. 274, No. 12, pp. 8029-8038, Mar. 19, 1999.
Memmi, L et al., "Protein-Calixarene Interactions: Complexation of Bovine Serum Albumin by Sulfonatoclix[*n*]arenas," Chemical Communications, No. 23, pp. 2474-2475, Dec. 7, 2001.
Kuo, Yu-Min et al., "Amyloid-β Peptides Interact with Plasma Proteins and Erthrocytes: Implications for their Quantitation in Plasmas," Biochemical and Biophysical Research Communications, Vo. 268, pp. 750-756, 200.
Yalpani, Manssur, "Polysaccharides: Syntheses, Modifications and Structures/Property Relations," pp. 27-32, 1988.
Sjogren, Magnus et al., "Advances in the Detection of Alzheimer's Disease-Use of Cerebrospinal Fluid Biomarkers," Clinica Chimica Acta, vol. 332, pp. 1-10, 2003.
Arduini, Arturo et al., "Calixarenes," pp. 145-173.
Da Silva, Eric et al., "Synthesis and Solid-State Structures of Mono-Functionalised Para-H-Calix-[6]-arenes," Journal of Supramolecular Chemistry, vol. 1, pp. 135-138, 2001.
Kumar et al., "The First Analogues of LNA (Locked Nucleic Acids): Phosphorothioate-LNA and 2'Thio-LNA," Biooganic & Medicinal Chemistry Letters 8, pp. 2219-2222, 1998.
Egholm et al., "Peptide Nucleic (PNA). Oligonucleotide Analogues with an Achiral Peptide Backbone," J. Am, Chem Soc.,vol. 114, pp. 1895-1897, 1992.
Madec et al., "Protease-resistant prion protein in brain and lymphoid organs of sheep within a naturally scrapie-infected flock." Microbial Pathogenesis, vol. 28, pp. 353-362, 2000.

(Continued)

*Primary Examiner* — Shafiqul Haq
*Assistant Examiner* — Galina Yakovleva
(74) *Attorney, Agent, or Firm* — Oliff & Berridge, PLC

(57) ABSTRACT

The present invention concerns a method for detecting aggregate-forming circulating protein forms in a biological sample of human origin that may contain said aggregate-forming circulating protein forms, characterized in that it uses a non-protein agent I producing aggregation of the circulating forms of the noninfectious proteins involved in pathological aggregation processes of the central nervous system and/or a non-protein agent II for capturing the natural aggregates of aggregate-forming circulating protein forms or the aggregates induced by said agents I.

14 Claims, 23 Drawing Sheets

OTHER PUBLICATIONS

Figures 2, 2A, 2B:
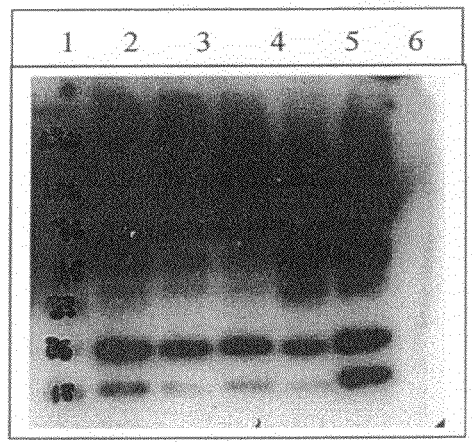

U. K. Laemmli, "Cleavage of structural Proteins during the Assembly of the Head of Bateriophage." Nature, vol. 227, pp. 680-685, Aug. 15, 1970.

Toulé et al., "Les aptàmeres: des ligands et des catalyseurs oligonculéotidiques obtenus par sélecxtion in vitro," Médecine/Sciences, vol. 14, pp. 155-66, 1998.

Prusiner et al., "Scrapie Prions Aggregate to Form Amyloid-like Birefringent Rods," Cell., vol. 35, No. 2 Pt. 1, pp. 349-358, Dec. 1983.

Meyer et al., "Detection of Bovine Spongiform Encephalopathy-Specific $PrP^{Sc}$ by Treatment with Heat and Guanidine Thiocyanate," Journal of Virology, vol. E73, No. 11, pp. 9386-9392, Nov. 1999.

Da Silva et al., "Synthesis and complexation properties towards amino acids of mono-substituted p-sulphonato-calix-[n]-arenes," Tetrahedron, vol. 59, No. 37, pp. 7357-7364, Sep. 2003.

Wang et al., "Cytotoxicity of Poly(Phenolic)Sulfonates and Theior Sodium Salts in L1210 Lymphoid Leukemia Cells," Metal Based Drugs, vol. 5, No. 3, pp. 147-159, 1998.

Arduini et al., "Macrocycle Synthesis," Eds. Harwood, L.M. & Moddy, C.J. Oxford University Press, (1996).

Koga et al., "Structural Regulation of a Peptide-Conjugated Graft Coploymer: A Simple Model for Amyloid Formation, "Chem. Eur. J., vol. 9, No. 5, pp. 1146-1156, 2003.

Jul. 12, 2010 Office Action issued in U.S. Appl. No. 12/457,535.

Dec. 11, 2009 Office Action issued in U.S. Appl. No. 12/457,535.

Jul. 6, 2005 International Search Report issued in International Application No. PCT/FR2005/000118.

\* cited by examiner

Figure 1

```
                              10                  20                  30
alpha-Synuclein    m l p g l a l l l l a a w t a r a l e V p t d g n a g l l a
APP                                                m i V f v r f n s s h g f
Parkin                             m a e p r q e f e V m e d h a g t y g l
Tau Protein 40                  50                  60
alpha-Synuclein
APP                e p q i a m f c g r l n m H m n v q n g k w d s d p s g t k
Parkin             p v e v d s - - d t s i f Q l k e v v a k r q g v p a d q l
Tau Protein        g d r k d q - - g g y t m H q - d q e g d t a g l k e s p 70                  80                  90
alpha-Synuclein
APP                t c i d T k e g i l q y c q e v y p E l q i t n v v e a n q
Parkin             r v i f A g k e l r n d w t v q n c D l d q q s i v h i v q
Tau Protein        l q t p T e d g s e e p g s e t - s D a k s t p t a e d v t 100                 110                 120
alpha-Synuclein              M d v f m K G - - - l S K a K e g v v a a A e k t k q
APP                p v t l I q n w c K r g r k q C K t H p h f v i p y r c l v g
Parkin             - - - - r p w r K G q e m n A t g g d d p r n a A g g c e r
Tau Protein        a p l V d e g a p G k q a a A Q p H t e i p e g t T a e e a 130                 140                 150
alpha-Synuclein    g v a e a A g k t k E g v l y V g s k t k e g - V V H g - -
APP                e f v s d A l l v p D k C k f L h q e r m d v c e t H l h -
Parkin             e p q s l T r V l d l s s S v l p g d s v g l a v I L H t -
Tau Protein        g i g d t p s L e d E a A g h V t q e p e s g k V V Q e g f 160                 170                 180
alpha-Synuclein    - - v A t v a e k T k E q v T N V - g g a V V t g v t a v a
APP                - w h T v a k e t C s E k s T N L h d y g M L l p c g i d k
Parkin             - - d S r k d s p p a g s p A G r s i y n s f y v y c k g p
Tau Protein        l r e p g p p g l S h Q l m S G M p g a p L L p e g p r e a 190                 200                 210
alpha-Synuclein    q K t V E - g A G s I a a a T g - - - - - f V K K d q L g k
APP                f R g V E f v C e p L l a e E S d - - - - - n V d s a d a e
Parkin             c Q r V Q - - p G k L l r v Q C s - - - - - t c R Q a t L t l
Tau Protein        t R q p s - g T G p e d t E g g r h a p e l L K H q l L g d 220                 230                 240
alpha-Synuclein    - n e E G a p - - - - - - q E - - - G i l E - - - D M p v D
APP                - - d d s d v w w g g a d t D y a d G s e D k v v E V a e E
Parkin             - - t Q G p s c w - - - - - d D - - v l i p n - - - r M s g E
Tau Protein        l h q E G p p l k g a g g k E r p - G s k E - - - E V d e D
```

Figure 1 (Follow.)

```
                            250                    260                     270
alpha-Synuclein      p D n e - - - a y E m p s - - - - - - E E G - - y Q d y e p
APP                  e E v a e v e e e E a d d d e d - - d E D G d e v E e e A e
Parkin               e q s p - - - - h e p g t - - - - - - s a e f f f k e g A h
Tau Protein          r D v d e s s p q D s p p s k a s p a Q D G r p p Q t a A r 280                    290                     300
alpha-Synuclein      E A
APP                  E p y e e a t e r T t s i a t t t t t t e s V e v v r e
Parkin               p T s d k e - - - T p v a l h l i a t n s r n I t e i t e t
Tau Protein          E A t s i p g f p A e g a i p l p v d f l s k V s t e i p a 310                    320                     330
alpha-Synuclein
APP                  v e s e q a e t g p C r a m i s r w y f d v t e g k e a p f
Parkin               d v r s p v l v f q C n s r - h v i e l d e f h l y e v t r
Tau Protein          s e p d g p s v g r A k g q d a p l e f t f - h v e i t p n 340                    350                     360
alpha-Synuclein
APP                  f y g g e g g n r n n f d t e e Y e m a v e g s a m s q s -
Parkin               l n d r q f v h d p q l g - - - Y s l p - e v a g e p n s -
Tau Protein          v q k e q a h s e e h l g r a a F p g a p g e g p e a r g p 370                    380                     390
alpha-Synuclein
APP                  - L l k t t Q e p l a r d p v k l p t t a a s t p d a v d k
Parkin               - L i k e l H h f r i l g - - e e q y n r y q q y g a e e e
Tau Protein          s L g e d t K e a d l p e p s e k q p a a a p r g k p v s r 400                    410                     420
alpha-Synuclein
APP                  y l E t p g d e n e H a h f q k a k e r l E a k h R e r m s
Parkin               v l Q m g g v l e p R p g e g a g l l p - E p d q R k v t e
Tau Protein          v p Q l k a r m v s K s k d g t g s d - - D k k a K t s t r 430                    440                     450
alpha-Synuclein
APP                  q v m r e w e e a e r q a k n l p k a d k k a v i q H f q e
Parkin               e - - - - - - g g n g l g e g f a f e r e e k e a y H e g e
Tau Protein          s s a k t l k n r p e l s p k l p t p g s s d p l i Q p s s 460                    470                     480
alpha-Synuclein
APP                  k v e s l E q e a A n e R q q l V e t H m a r v e a m l n d
Parkin               e s a v f E a s g T t Q a y r V d e R a a e q a r w e a a
Tau Protein          p a v e p E p p s S p k H v s s V t s R t g s s g a k e m k
```

Figure 1 (Follow.)

```
                            490                       500                     510
alpha-Synuclein
APP              r R r l a l e N y i t A l Q a v p F r p R - - - H v f n M
Parkin           s K c t i k k T t k p C p R c h v P v e K - - - N g g c M
Tau Protein      l K g a d g k T k i a T p R g a a P g Q k g q a N a t r l 520                       530                     540
alpha-Synuclein
APP              l k K y v r a e q k - - d r q h t l k h f e H v r m v d p k
Parkin           h m K c p q p q c r l c w c w n c g c e w n R v c m g d h w
Tau Protein      p a K t p p a p k t p p s s g e p p k s g d R s g y s s p g 550                       560                     570
alpha-Synuclein
APP              k a a q i r s q v m t - h l r v i y e r m n q s l s l l y n
Parkin           f d v
Tau Protein      s p g t p g s r s r t p s l p t p p t r e p k k v a v v r t 580                       590                     600
alpha-Synuclein
APP              v p a v a e e i q d e v d e l l q k e q n y s d d v l a n m
Parkin
Tau Protein      p p k s p s s a k s r l q t a p v p - m p d l k n v k s k i 610                       620                     630
alpha-Synuclein
APP              i s e p r i s y g n d a l m p s l t e t k t t v e l l p v n
Parkin
Tau Protein      g s t e n l k h q p g g g k v q i i n k k - - l d l s n v q 640                       650                     660
alpha-Synuclein
APP              g e f s l d d l q p w h s f g a d s v p a n t e n e v e p v
Parkin
Tau Protein      s k c g s k d n i k h v p g g g s v q i v y k p v d l s k v 670                       680                     690
alpha-Synuclein
APP              d a r p a a d r g l t t r p g s g l t n i k t e e i s e v k
Parkin
Tau Protein      t s k c g s l g n i h h k p g g g q v e v k s e k l - d f k 700                       710                     720
alpha-Synuclein
APP              m d a e f r h d s g y e v h h q k l v f f a e d v g s n k g
Parkin
Tau Protein      d r v q s k i g s - l d n i t h v p g g g n k k i e t h k l
```

Figure 1 (Follow.)

```
                           730                   740                   750
alpha-Synuclein
APP                a i i g l m v g g v v i a t v i v i t l v m l k k k q y t s
Parkin
Tau Protein        t f r e n a k a k t d h g a e i v y k s p v v s g d t s p r 760                   770                   780
alpha-Synuclein
APP                i h h g v v e v d a a v t p e e r h l s k m q q n g y e n p
Parkin
Tau Protein        h l s n v s s t g s i d m v d s p q l a t l a d e v s a s l 790                   800                   810
alpha-Synuclein
APP                t y k f f e q m q n
Parkin
Tau Protein        a k q g l
```

Expected specific bands (60 000 Da) ▬
Nonspecific bands ▩
Specific bands dues
to degradation products ⋯

FIGURE 3
Figure 3A
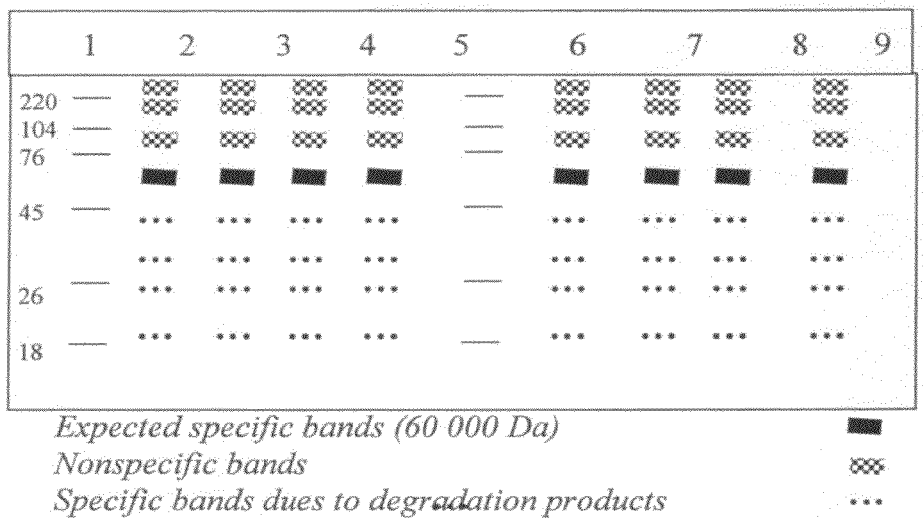
Expected specific bands (60 000 Da)
Nonspecific bands
Specific bands dues to degradation products
Figure 3B
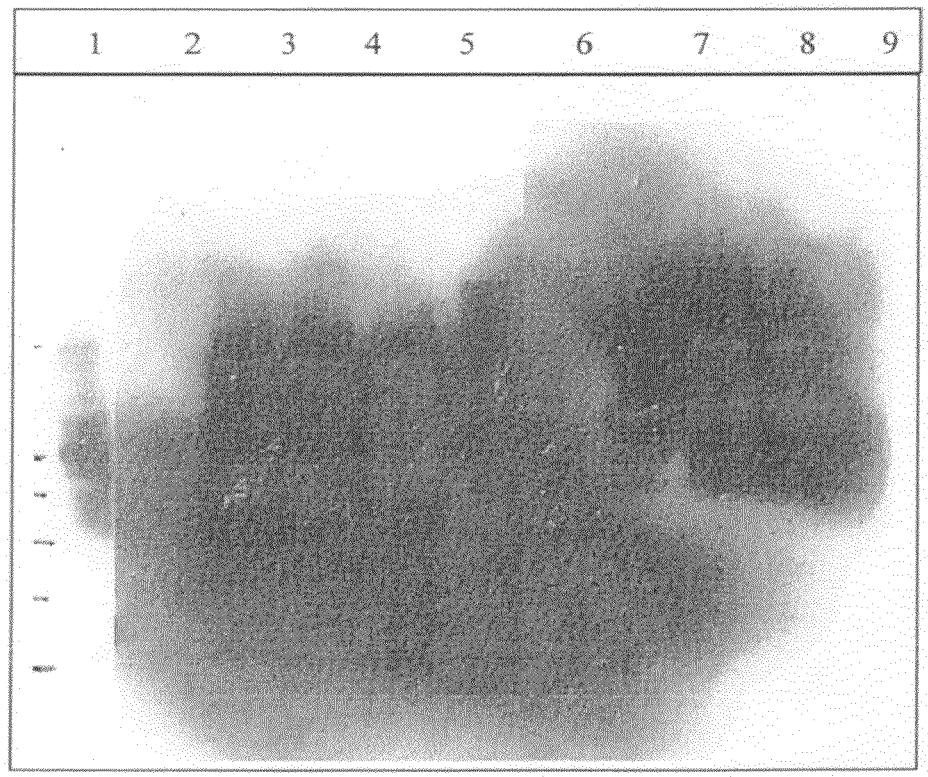

FIGURE 4
Figure 4A
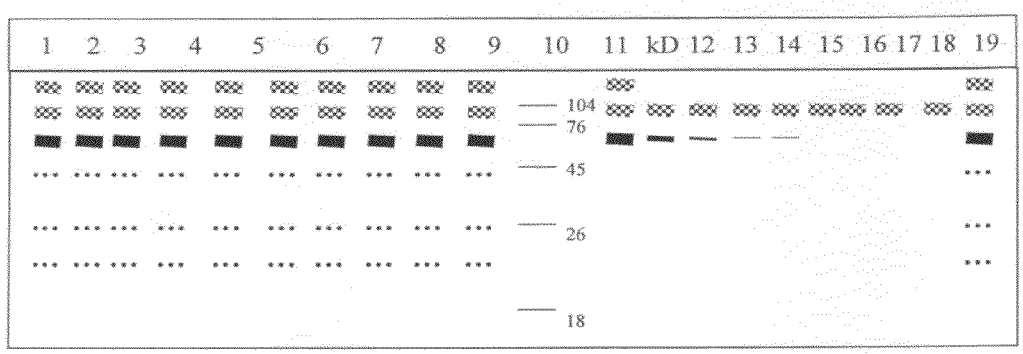
Expected specific bands (60 000 Da)
Nonspecific bands
Specific bands dues to degradation products
Figure 4B
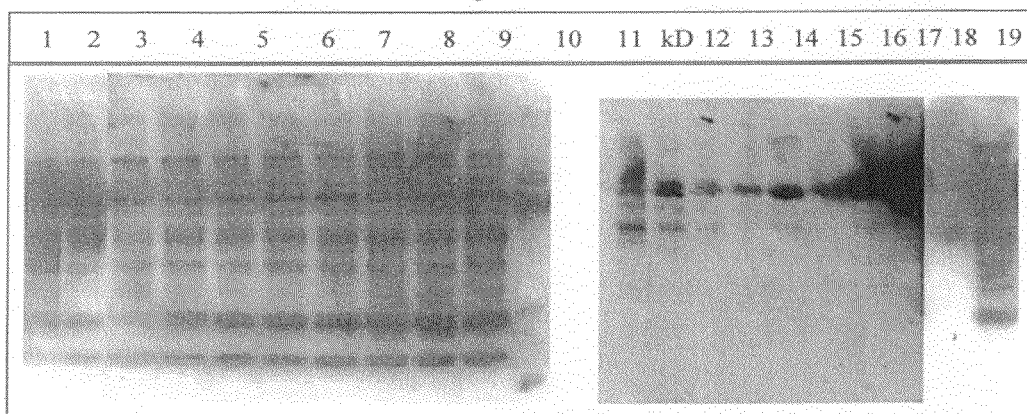

FIGURE 5
Figure 5A
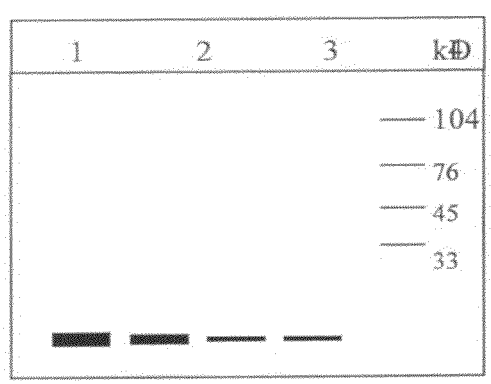
Figure 5B
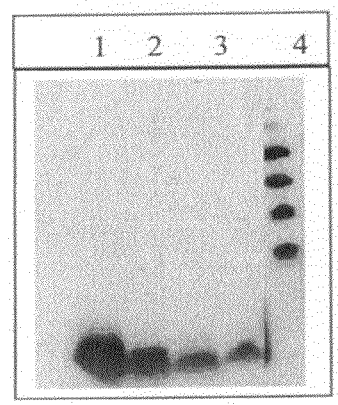

FIGURE 6
Figure 6A
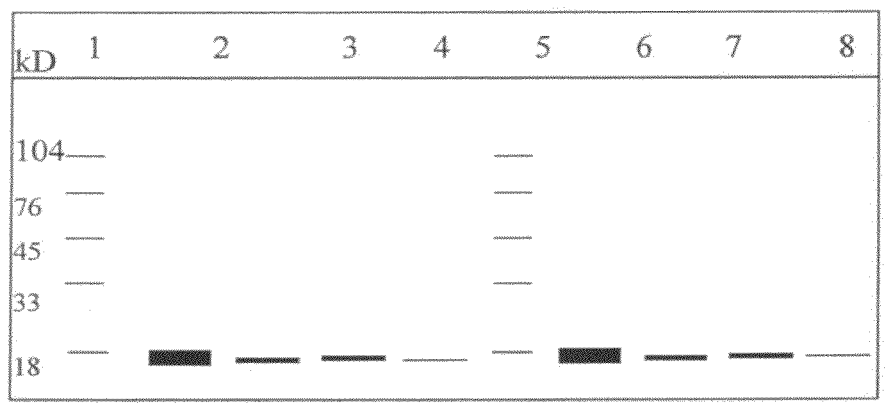
Figure 6B
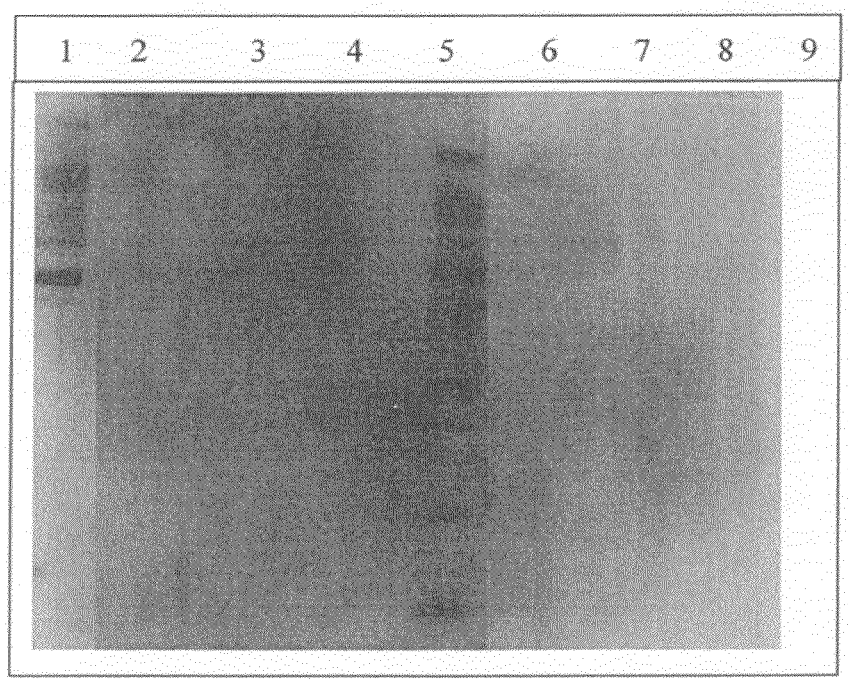

FIGURE 7
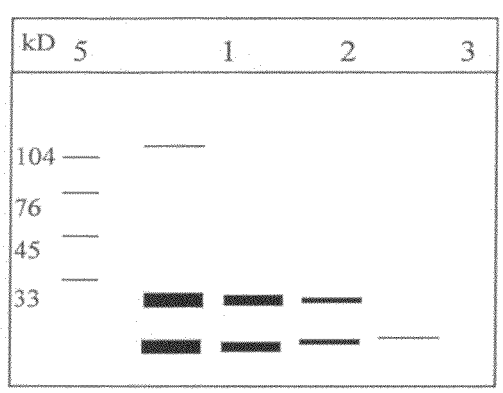
Figure 7A
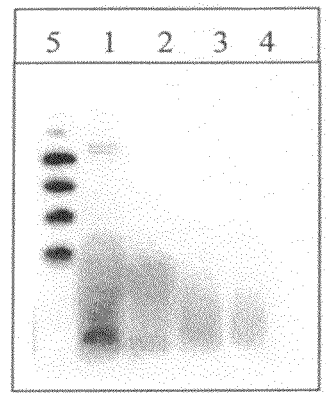
Figure 7B

FIGURE 8
Figure 8A
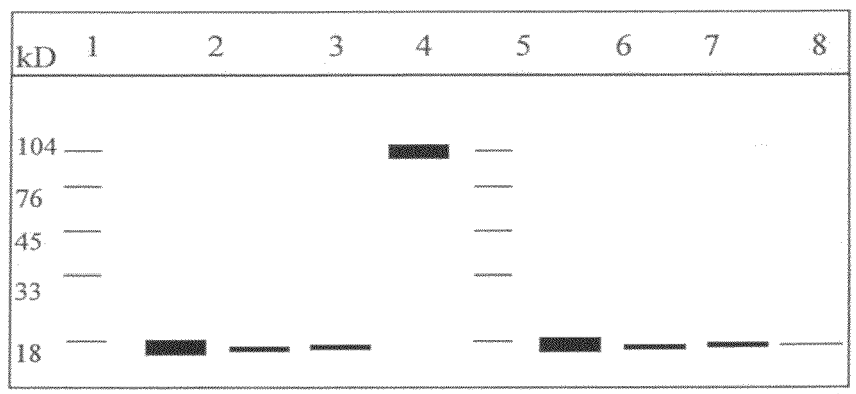
Figure 8B
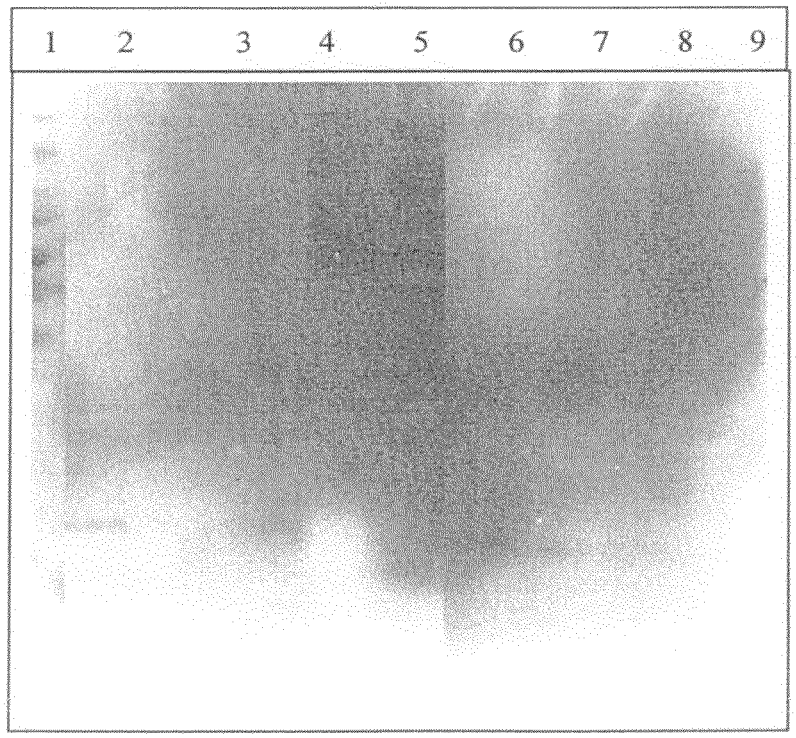

FIGURE 15
Figure 15A
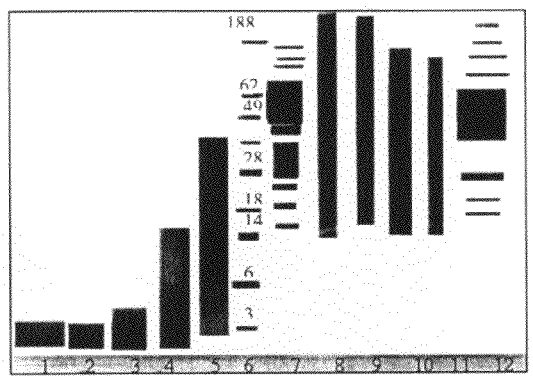
Figure 15B
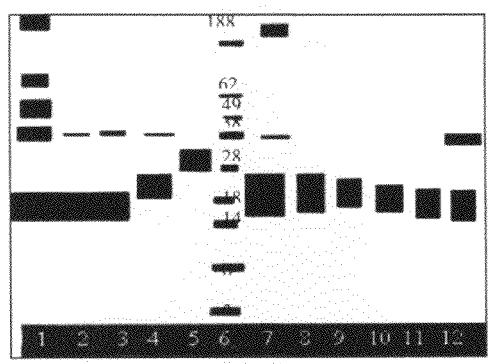
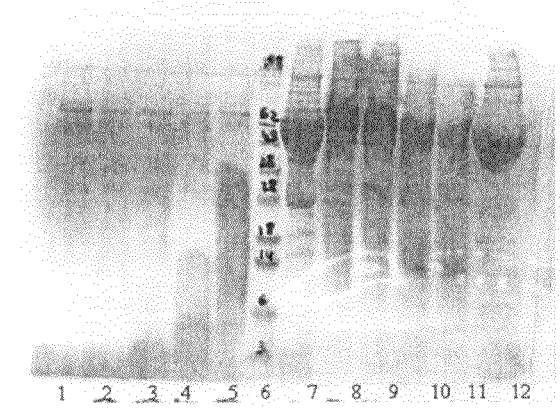
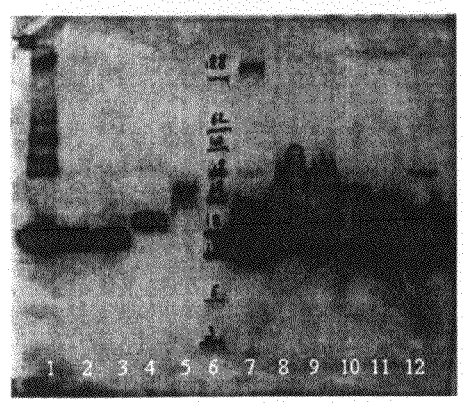

FIGURE 16
Figure 16A
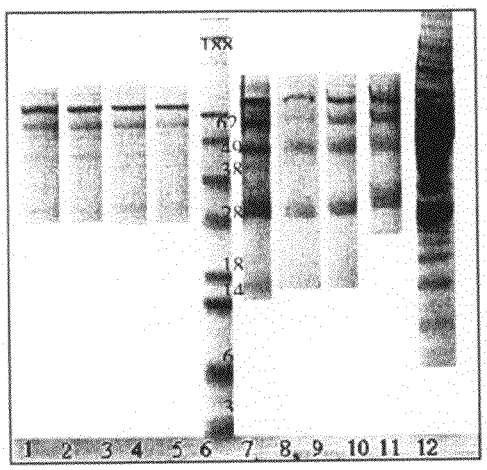
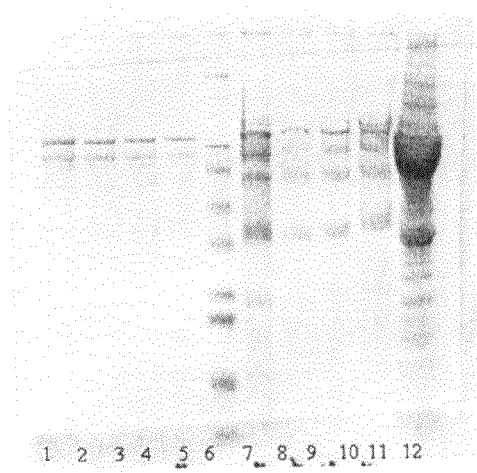
Figure 16B
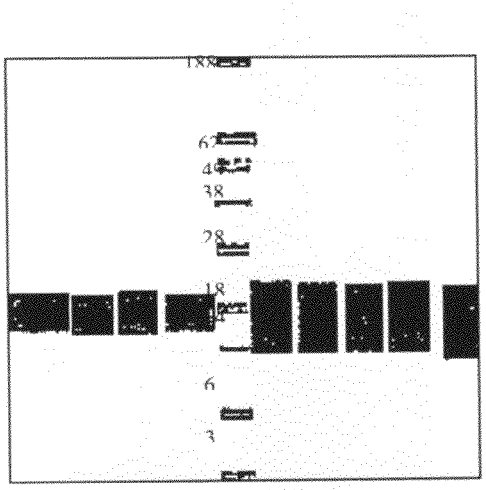
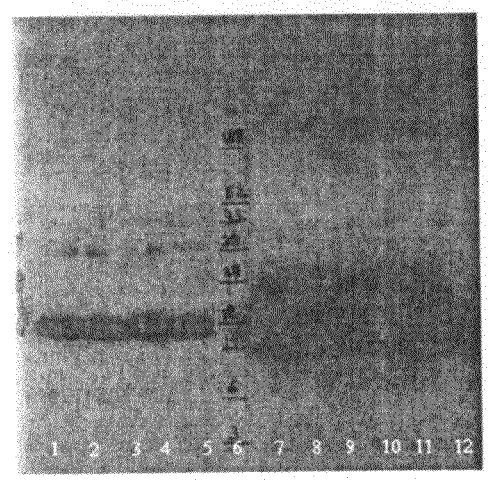

FIGURE 17
Figure 17A
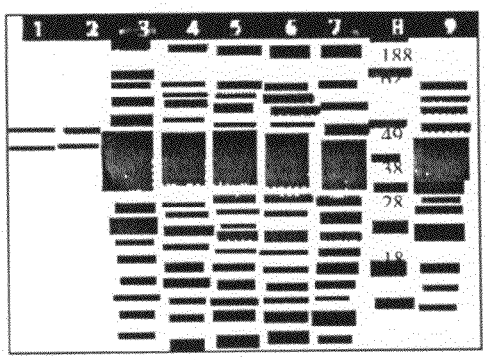
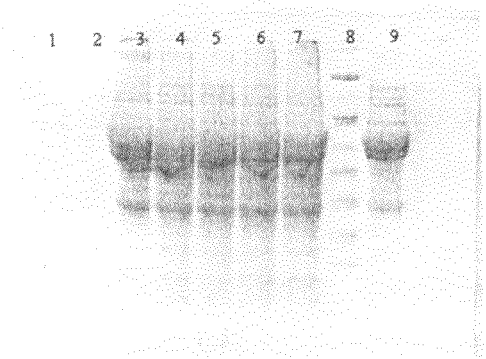
Figure 17B
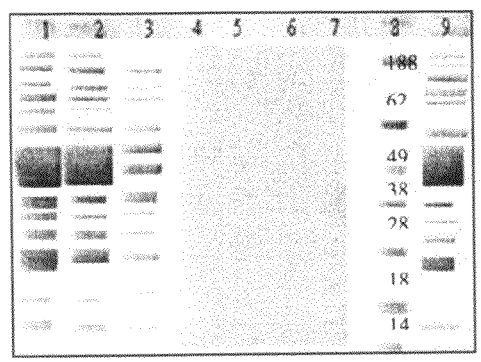
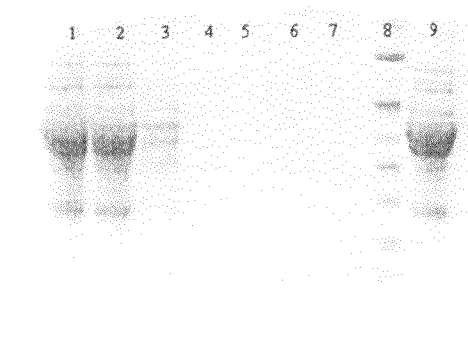

FIGURE 18
Figure 18A
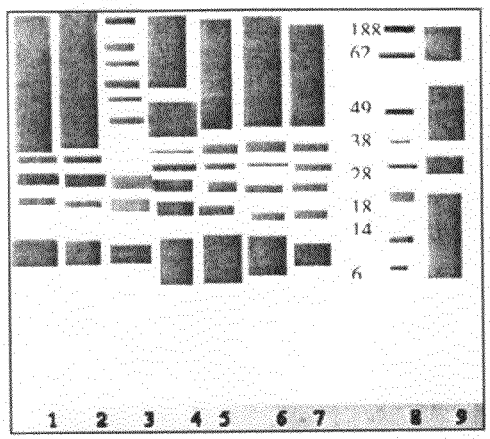
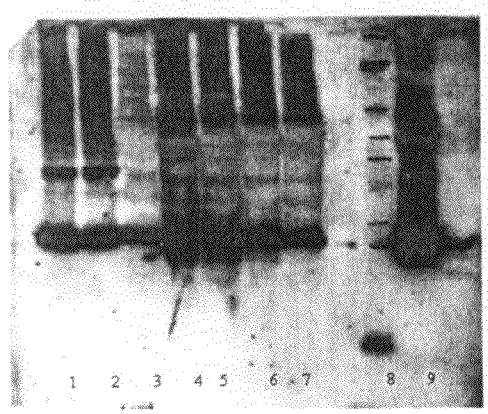
Figure 18B
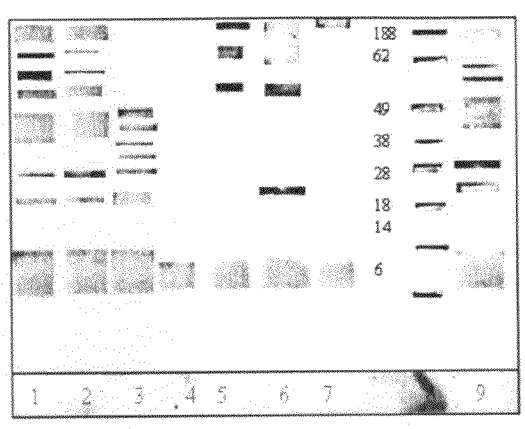
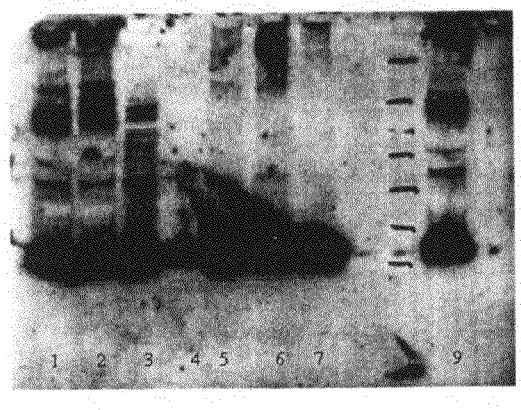

FIGURE 19
Figure 19A
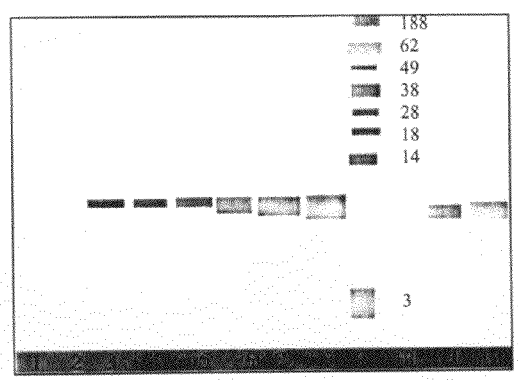
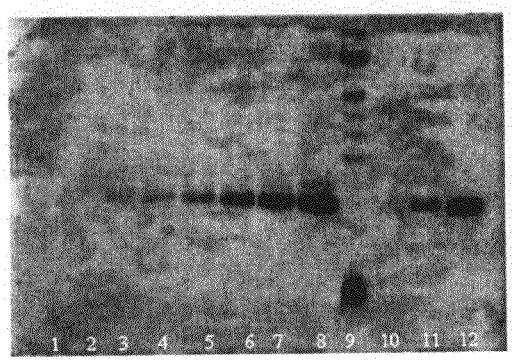
Figure 19B
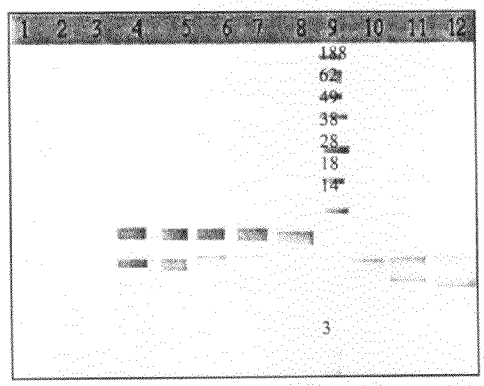
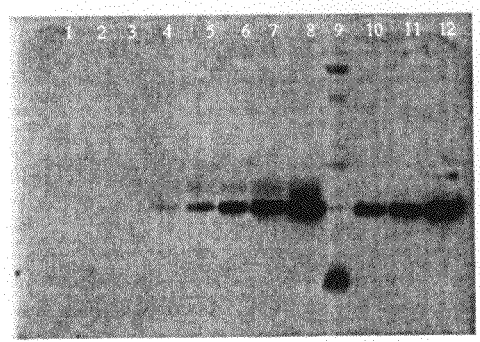

SEQUENCE LISTING

<160> NUMBER OF SEQ ID NOS: 6

<210> SEQ ID NO 1
<211> LENGTH: 140
<212> TYPE: PRT
<213> ORGANISM: human

<400> SEQUENCE: 1

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140

<210> SEQ ID NO 2
<211> LENGTH: 770
<212> TYPE: PRT
<213> ORGANISM: human

<400> SEQUENCE: 2

Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

-continued

```
Asp Lys Phe Arg Gly Val Glu Phe Val Cys Cys Pro Leu Ala Glu
            180                 185                 190

Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Thr Glu Ser Val Glu Glu Val Val Arg
        275                 280                 285

Glu Val Cys Ser Glu Gln Ala Glu Thr Gly Pro Cys Arg Ala Met Ile
    290                 295                 300

Ser Arg Trp Tyr Phe Asp Val Thr Glu Gly Lys Cys Ala Pro Phe Phe
305                 310                 315                 320

Tyr Gly Gly Cys Gly Gly Asn Arg Asn Asn Phe Asp Thr Glu Glu Tyr
                325                 330                 335

Cys Met Ala Val Cys Gly Ser Ala Met Ser Gln Ser Leu Leu Lys Thr
            340                 345                 350

Thr Gln Glu Pro Leu Ala Arg Asp Pro Val Lys Leu Pro Thr Thr Ala
        355                 360                 365

Ala Ser Thr Pro Asp Ala Val Asp Lys Tyr Leu Glu Thr Pro Gly Asp
    370                 375                 380

Glu Asn Glu His Ala His Phe Gln Lys Ala Lys Glu Arg Leu Glu Ala
385                 390                 395                 400

Lys His Arg Glu Arg Met Ser Gln Val Met Arg Glu Trp Glu Glu Ala
                405                 410                 415

Glu Arg Gln Ala Lys Asn Leu Pro Lys Ala Asp Lys Lys Ala Val Ile
            420                 425                 430

Gln His Phe Gln Glu Lys Val Glu Ser Leu Glu Gln Glu Ala Ala Asn
        435                 440                 445

Glu Arg Gln Gln Leu Val Glu Thr His Met Ala Arg Val Glu Ala Met
    450                 455                 460

Leu Asn Asp Arg Arg Arg Leu Ala Leu Glu Asn Tyr Ile Thr Ala Leu
465                 470                 475                 480

Gln Ala Val Pro Pro Arg Pro Arg His Val Phe Asn Met Leu Lys Lys
                485                 490                 495

Tyr Val Arg Ala Glu Gln Lys Asp Arg Gln His Thr Leu Lys His Phe
            500                 505                 510

Glu His Val Arg Met Val Asp Pro Lys Lys Ala Ala Gln Ile Arg Ser
        515                 520                 525

Gln Val Met Thr His Leu Arg Val Ile Tyr Glu Arg Met Asn Gln Ser
    530                 535                 540

Leu Ser Leu Leu Tyr Asn Val Pro Ala Val Ala Glu Glu Ile Gln Asp
545                 550                 555                 560

Glu Val Asp Glu Leu Leu Gln Lys Glu Gln Asn Tyr Ser Asp Asp Val
                565                 570                 575

Leu Ala Asn Met Ile Ser Glu Pro Arg Ile Ser Tyr Gly Asn Asp Ala
            580                 585                 590

Leu Met Pro Ser Leu Thr Glu Thr Lys Thr Thr Val Glu Leu Leu Pro
        595                 600                 605
```

```
Val Asn Gly Glu Phe Ser Leu Asp Asp Leu Gln Pro Trp His Ser Phe
    610                 615                 620
Gly Ala Asp Ser Val Pro Ala Asn Thr Glu Asn Glu Val Glu Pro Val
625                 630                 635                 640
Asp Ala Arg Pro Ala Ala Asp Arg Gly Leu Thr Thr Arg Pro Gly Ser
                645                 650                 655
Gly Leu Thr Asn Ile Lys Thr Glu Glu Ile Ser Glu Val Lys Met Asp
                660                 665                 670
Ala Glu Phe Arg His Asp Ser Gly Tyr Glu Val His His Gln Lys Leu
                675                 680                 685
Val Phe Phe Ala Glu Asp Val Gly Ser Asn Lys Gly Ala Ile Ile Gly
                690                 695                 700
Leu Met Val Gly Gly Val Val Ile Ala Thr Val Ile Val Ile Thr Leu
705                 710                 715                 720
Val Met Leu Lys Lys Lys Gln Tyr Thr Ser Ile His His Gly Val Val
                725                 730                 735
Glu Val Asp Ala Ala Val Thr Pro Glu Glu Arg His Leu Ser Lys Met
                740                 745                 750
Gln Gln Asn Gly Tyr Glu Asn Pro Thr Tyr Lys Phe Phe Glu Gln Met
                755                 760                 765
Gln Asn
    770

<210> SEQ ID NO 3
<211> LENGTH: 465
<212> TYPE: PRT
<213> ORGANISM: human

<400> SEQUENCE: 3

Met Ile Val Phe Val Arg Phe Asn Ser Ser His Gly Phe Pro Val Glu
1               5                   10                  15
Val Asp Ser Asp Thr Ser Ile Phe Gln Leu Lys Glu Val Val Ala Lys
                20                  25                  30
Arg Gln Gly Val Pro Ala Asp Gln Leu Arg Val Ile Phe Ala Gly Lys
            35                  40                  45
Glu Leu Arg Asn Asp Trp Thr Val Gln Asn Cys Asp Leu Asp Gln Gln
50                  55                  60
Ser Ile Val His Ile Val Gln Arg Pro Trp Arg Lys Gly Gln Glu Met
65                  70                  75                  80
Asn Ala Thr Gly Gly Asp Asp Pro Arg Asn Ala Ala Gly Gly Cys Glu
                85                  90                  95
Arg Glu Pro Gln Ser Leu Thr Arg Val Asp Leu Ser Ser Ser Val Leu
            100                 105                 110
Pro Gly Asp Ser Val Gly Leu Ala Val Ile Leu His Thr Asp Ser Arg
        115                 120                 125
Lys Asp Ser Pro Pro Ala Gly Ser Pro Ala Gly Arg Ser Ile Tyr Asn
    130                 135                 140
Ser Phe Tyr Val Tyr Cys Lys Gly Pro Cys Gln Arg Val Gln Pro Gly
145                 150                 155                 160
Lys Leu Arg Val Gln Cys Ser Thr Cys Arg Gln Ala Thr Leu Thr Leu
                165                 170                 175
Thr Gln Gly Pro Ser Cys Trp Asp Asp Val Leu Ile Pro Asn Arg Met
            180                 185                 190
Ser Gly Glu Cys Gln Ser Pro His Cys Pro Gly Thr Ser Ala Glu Phe
        195                 200                 205
```

```
Phe Phe Lys Cys Gly Ala His Pro Thr Ser Asp Lys Glu Thr Pro Val
    210                 215                 220

Ala Leu His Leu Ile Ala Thr Asn Ser Arg Asn Ile Thr Cys Ile Thr
225                 230                 235                 240

Cys Thr Asp Val Arg Ser Pro Val Leu Val Phe Gln Cys Asn Ser Arg
                245                 250                 255

His Val Ile Cys Leu Asp Cys Phe His Leu Tyr Cys Val Thr Arg Leu
            260                 265                 270

Asn Asp Arg Gln Phe Val His Asp Pro Gln Leu Gly Tyr Ser Leu Pro
        275                 280                 285

Cys Val Ala Gly Cys Pro Asn Ser Leu Ile Lys Glu Leu His His Phe
290                 295                 300

Arg Ile Leu Gly Glu Glu Gln Tyr Asn Arg Tyr Gln Gln Tyr Gly Ala
305                 310                 315                 320

Glu Glu Cys Val Leu Gln Met Gly Gly Val Leu Cys Pro Arg Pro Gly
                325                 330                 335

Cys Gly Ala Gly Leu Leu Pro Glu Pro Asp Gln Arg Lys Val Thr Cys
            340                 345                 350

Glu Gly Gly Asn Gly Leu Gly Cys Gly Phe Ala Phe Cys Arg Glu Cys
        355                 360                 365

Lys Glu Ala Tyr His Glu Gly Glu Cys Ser Ala Val Phe Glu Ala Ser
370                 375                 380

Gly Thr Thr Thr Gln Ala Tyr Arg Val Asp Glu Arg Ala Ala Glu Gln
385                 390                 395                 400

Ala Arg Trp Glu Ala Ala Ser Lys Glu Thr Ile Lys Lys Thr Thr Lys
                405                 410                 415

Pro Cys Pro Arg Cys His Val Pro Val Glu Lys Asn Gly Gly Cys Met
            420                 425                 430

His Met Lys Cys Pro Gln Pro Gln Cys Arg Leu Glu Trp Cys Trp Asn
        435                 440                 445

Cys Gly Cys Glu Trp Asn Arg Val Cys Met Gly Asp His Trp Phe Asp
    450                 455                 460

Val
465

<210> SEQ ID NO 4
<211> LENGTH: 758
<212> TYPE: PRT
<213> ORGANISM: human

<400> SEQUENCE: 4

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
                85                  90                  95

Ile Pro Glu Gly Thr Thr Ala Glu Glu Ala Gly Ile Gly Asp Thr Pro
            100                 105                 110
```

```
Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Pro Gly
130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly Pro Pro Leu Lys Gly Ala Gly Gly
        195                 200                 205

Lys Glu Arg Pro Gly Ser Lys Glu Glu Val Asp Glu Asp Arg Asp Val
210                 215                 220

Asp Glu Ser Ser Pro Gln Asp Ser Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
        275                 280                 285

Val Gly Arg Ala Lys Gly Gln Asp Ala Pro Leu Glu Phe Thr Phe His
    290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
            340                 345                 350

Glu Pro Ser Glu Lys Gln Pro Ala Ala Ala Pro Arg Gly Lys Pro Val
        355                 360                 365

Ser Arg Val Pro Gln Leu Lys Ala Arg Met Val Ser Lys Ser Lys Asp
    370                 375                 380

Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Pro Lys Leu Pro Thr
                405                 410                 415

Pro Gly Ser Ser Asp Pro Leu Ile Gln Pro Ser Ser Pro Ala Val Cys
            420                 425                 430

Pro Glu Pro Pro Ser Ser Pro Lys His Val Ser Ser Val Thr Ser Arg
        435                 440                 445

Thr Gly Ser Ser Gly Ala Lys Glu Met Lys Leu Lys Gly Ala Asp Gly
    450                 455                 460

Lys Thr Lys Ile Ala Thr Pro Arg Gly Ala Ala Pro Gly Gln Lys
465                 470                 475                 480

Gly Gln Ala Asn Ala Thr Arg Ile Pro Ala Lys Thr Pro Pro Ala Pro
                485                 490                 495

Lys Thr Pro Pro Ser Ser Gly Pro Pro Lys Ser Gly Asp Arg Ser
            500                 505                 510

Gly Tyr Ser Ser Pro Gly Ser Pro Gly Thr Pro Gly Ser Arg Ser Arg
        515                 520                 525

Thr Pro Ser Leu Pro Thr Pro Pro Thr Arg Glu Pro Lys Lys Val Ala
```

```
                    530                 535                 540
Val Val Arg Thr Pro Pro Lys Ser Pro Ser Ala Lys Ser Arg Leu
545                 550                 555                 560

Gln Thr Ala Pro Val Pro Met Pro Asp Leu Lys Asn Val Lys Ser Lys
                    565                 570                 575

Ile Gly Ser Thr Glu Asn Leu Lys His Gln Pro Gly Gly Gly Lys Val
                580                 585                 590

Gln Ile Ile Asn Lys Lys Leu Asp Leu Ser Asn Val Gln Ser Lys Cys
                595                 600                 605

Gly Ser Lys Asp Asn Ile Lys His Val Pro Gly Gly Gly Ser Val Gln
610                 615                 620

Ile Val Tyr Lys Pro Val Asp Leu Ser Lys Val Thr Ser Lys Cys Gly
625                 630                 635                 640

Ser Leu Gly Asn Ile His His Lys Pro Gly Gly Gln Val Glu Val
                645                 650                 655

Lys Ser Glu Lys Leu Asp Phe Lys Asp Arg Val Gln Ser Lys Ile Gly
                660                 665                 670

Ser Leu Asp Asn Ile Thr His Val Pro Gly Gly Gly Asn Lys Lys Ile
                675                 680                 685

Glu Thr His Lys Leu Thr Phe Arg Glu Asn Ala Lys Ala Lys Thr Asp
690                 695                 700

His Gly Ala Glu Ile Val Tyr Lys Ser Pro Val Val Ser Gly Asp Thr
705                 710                 715                 720

Ser Pro Arg His Leu Ser Asn Val Ser Ser Thr Gly Ser Ile Asp Met
                725                 730                 735

Val Asp Ser Pro Gln Leu Ala Thr Leu Ala Asp Glu Val Ser Ala Ser
                740                 745                 750

Leu Ala Lys Gln Gly Leu
                755

<210> SEQ ID NO 5
<211> LENGTH: 40
<212> TYPE: PRT
<213> ORGANISM: human

<400> SEQUENCE: 5

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
                20                  25                  30

Gly Leu Met Val Gly Gly Val Val
            35                  40

<210> SEQ ID NO 6
<211> LENGTH: 42
<212> TYPE: PRT
<213> ORGANISM: human

<400> SEQUENCE: 6

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
                20                  25                  30

Gly Leu Met Val Gly Gly Val Val Ile Ala
            35                  40
```

METHOD FOR DETECTING AGGREGATE-FORMING CIRCULATING PROTEIN FORMS USING AN AGENT FOR AGGREGATING SAID FORMS AND AN AGENT FOR CAPTURING FORMED AGGREGATES

The present invention relates to the field of neurodegenerative diseases recognized as noninfectious to date, and in particular to a method for detecting aggregate-forming circulating protein forms associated with these diseases.

The increase in age-related diseases increasingly affects our populations, the average age of which has greatly increased over the last century. Some of these diseases affect the brain and appear to affect all cognitive functions. There can also be considerable effects on sensory-motor functions in some of these diseases. These are the "neurodegenerative" diseases, recognized as noninfectious to date, such as Parkinson's disease, Alzheimer's disease, tauopathies, dementia with Lewy bodies, Huntington's disease and vascular dementia.

Thus, for example, more than 25 million people in the world suffer from Alzheimer's disease. In France, close to 800 000 people suffer from Alzheimer's disease or from related diseases. In addition, the demographic aging of the population is becoming accentuated and will result in an increase in this number. There are already close to 165 000 new sufferers per year. Alzheimer's disease represents the fourth most common cause of mortality, after cardiovascular conditions, cancers and strokes. This neurodegenerative dementia progressively and irreversibly results in memory loss (amnesia) and loss of cognitive functions (aphasia, apraxia, agnosia).

Like Alzheimer's disease, the main noninfectious neurodegenerative diseases are characterized by extracellular and/or intracellular deposits consisting of noninfectious proteins which may be present in circulating form (aggregate-forming circulating protein forms) and are involved in pathological aggregation processes of the central nervous system. These proteins may undergo spontaneous conformational modifications, induced by cofactors or enzymes, or else by genetic mutations which promote their spontaneous aggregation in the form of protein deposits; these modifications lead to an accumulation in various areas of the brain, according to the type of protein and the physiopathological circumstances (El-Agnaf O et al., 2003, Lancet Neurol, 2: 461-462).

Thus, in the case of Alzheimer's disease, the aggregated proteins are mainly the Tau protein and fragments of the APP protein (Amyloid Precursor Protein), the beta-amyloid peptides (beta 1-40, beta 1-41, beta 1-42, for example). The Tau protein is also associated with tauopathies, which are non-Alzheimer dementias associated with deposits of aggregated Tau protein in the brain in the absence of beta-amyloid protein. The APP protein and/or its beta-amyloid peptide fragments are also associated with vascular dementias, characterized by perivascular deposits of amyloid aggregates. In the case of Parkinson's disease, characterized by a neuronal degeneration in the central gray nuclei, an associated protein is Parkin, in particular for the familial forms, and also alpha-Synuclein. The latter is also implicated in Parkinsonian dementia, which can occur in addition to the sensory-motor problems. Alpha-synuclein is also associated with dementia with Lewy bodies. The latter are characterized by a deposit of aggregated alpha-synuclein protein, in particular in areas of the frontal cortex, which generates neuronal degeneration, with cognitive functions being affected, resulting in a dementia syndrome. In the case of Huntington's disease, the aggregating protein is Huntingtin. Thus, this phenomenon of cerebral deposits of neurotoxic protein aggregates is found in most neurodegenerative diseases but, unlike "prion" diseases, the proteins associated with neurodegenerative diseases do not exhibit infectious properties and are not therefore transmissible. In fact, "prion" proteins are the agents that vector transmissible spongiform encephalopathies and this disease can be transmitted by injection of these pathogenic prions isolated in sick individuals; this is also valid for prion diseases of genetic origin, such as Gertsmann-Straüssler-Scheinker (GSS) disease, the pathological prion of which is initiated by the host's genetic mutations, but the pathological protein of which, once formed, acquires infectious properties specific to prion diseases (Lantos P L., 1992, Histopathology, 20(1): 1-11). "Prion diseases" result from the gradual increase in the amount of pathogenic prion protein in the individual inoculated or contaminated with the latter, or else carrying the genetic mutations capable of initiating the pathological conversion of the normal protein, thus creating an "endogenous" infection.

The proteins associated with noninfectious neurodegenerative diseases differ in particular from the latter by virtue of their inability to transmit the disease to a normal individual by systemic injection. Similarly, no tissue element derived from these noninfectious neurodegenerative diseases has been able to transmit the disease, thereby excluding the latter from being infectious diseases, unlike prion diseases.

The current diagnosis of these noninfectious neurodegenerative diseases is most commonly based on imaging, which supplements the clinical and neuropsychological examination. It is a laborious and expensive procedure which requires several diagnostic steps, none being carried out on a biological sample. In some cases, a mutation of genetic origin is the cause of the abnormal aggregation of one of these proteins, and a genetic diagnosis at the DNA sequence level is possible, but this remains uncommon with regard to the "nongenetic" forms.

An easier and faster diagnosis for these diseases is therefore necessary. Diagnosis in biological samples, in humans, therefore becomes extremely important. In particular, their immunological detection would allow a simpler, even earlier, diagnosis with an obvious gain in terms of therapeutic steps to be initiated before spread of the lesions (El-Agnaf O et al., 2003, above).

Various teams have endeavored to achieve such a detection in biological samples. Thus, patent application EP 713 095 describes the diagnosis, in the cerebrospinal fluid (CSF), of a patient suffering from Alzheimer's disease by measuring the amount of a β-Amyloid peptide, optionally in combination with measuring the amount of Tau protein, in comparison with a predetermined value. This method has the drawback that it has been demonstrated only for CSF and that the detection of β-Amyloid peptide must be supplemented with an assay of Tau protein, in order to improve the specificity of the test (Sjogren M et al., 2003, Clin Chim Acta, 332:1-10).

No routine blood test exists at the current time for the biological diagnosis of these noninfectious neurodegenerative diseases. For example the Tau protein is difficult to detect in the blood, since it is produced only in neurons and is very dilute in the blood, after passage into the CSF. Moreover, in the latter, the Tau protein is more or less well detected by the existing tests. The assaying of the APP protein and of its circulating fragments, including the precursor protein, can be carried out in blood platelets, but this also remains problematic since many aggregate-forming circulating protein forms are bound to plasma proteins which can mask epitopes and thus render them undetectable and/or impossible to capture with antibodies directed against these same epitopes. It is therefore impossible, since the masked epitopes are those which are recognized by the antibodies used, to use conventional immunoenzymatic procedures of "sandwich ELISA" type. Furthermore, antibodies are very large proteins which cannot gain access to molecular sites of aggregate-forming circulating protein forms if the latter are internalized in a three-dimensional network, as is the case in the aggregated forms and in the forms associated with plasma ligands. Only small molecules can interact with an increased number of proteins in these aggregated aggregate-forming circulating protein forms, whereas antibodies will more readily detect the free forms that are not aggregated and not associated with plasma ligands, i.e. the most physiological fraction of these proteins associated with neurodegenerative diseases. Thus, a variable fraction, the significance of which consequently remains unverifiable, cannot be assayed by standard immunoassays (Kuo Y et al., 2000, Biochem Biophys Res Commun, 268:750-756).

Consequently, the prior art methods constantly come up against the difficulty of capturing, concentrating and/or detecting the soluble and/or circulating forms of the proteins associated with noninfectious neurodegenerative pathologies. Methods suitable for each type of protein are sometimes envisioned, but, in addition to the fact that they are difficult to transpose to a large-scale routine test, they do not make it possible to carry out a single method, common to all these proteins, or to a sufficient number of proteins that would be diagnostically acceptable (Kuo Y et al., 2000, above).

A method capable of collecting these proteins, of separating them from the biological fluids without involving antibody recognition, and then optionally of treating them so as to dissociate the possible ligands under conditions compatible with them being fixed on surfaces suitable for immunoenzymatic assays and, subsequently, of finally identifying them with antibodies, would make it possible to carry out an effective and comparable detection of these various proteins. Such conditions would even be able to allow a more effective isolation of all these proteins and of their various circulating forms, with an even interpretation of the assays which gives a better correlation of the real bioclinical parameters, and therefore the respective diagnoses of these diseases.

U.S. Pat. No. 6,365,414 describes an in vitro method for detecting the formation of beta-amyloid peptides, using heavy metal cations such as zinc. However, due to the small number of zinc-binding sites on the proteins, this technique does not make it possible to aggregate and concentrate the beta-amyloid peptides by forming multimolecular networks that can be sedimented by low-speed centrifugation.

Patent application WO 03/073106 describes a method for the selective binding of the pathological forms of the prion, amyloid and Tau proteins. In particular, the capture of the aggregated form of the Tau protein by dextran sulfate is described in one of the examples of this application. That document does not mention the use of an aggregating agent, and dextran sulfate belongs neither to the glycosaminoglycan family nor to the family of macrocyclic molecules.

The present inventors have now demonstrated, against all expectations, that the use of a non-protein agent I producing aggregation of the circulating forms of the noninfectious proteins involved in pathological aggregation processes of the central nervous system and/or of a non-protein agent II for capturing the natural aggregates of aggregation-forming circulating protein forms or the aggregates induced by said agents I, in a test for the diagnosis of aggregate-forming circulating protein forms associated with noninfectious neurodegenerative diseases, makes it possible to detect, according to a single method, these protein forms at dilutions and under conditions where they are not detectable with the methods currently used. The use of these two agents alone or in combination can clearly improve, but in any case does not prevent, the ability of the aggregate-forming protein forms to bind to a binding partner specific for these aggregate-forming protein forms, which binding partner is used in the diagnostic test.

Thus, a subject of the present invention is a method for detecting, in vitro, at least one aggregate-forming circulating protein form associated with noninfectious neurodegenerative diseases in a biological sample of human origin, characterized in that it uses a non-protein agent I producing aggregation of the circulating forms of the noninfectious proteins involved in the pathological aggregation processes of the central nervous system and/or a non-protein agent II for capturing the natural aggregates of aggregate-forming circulating protein forms or the aggregates induced by said agents I.

The invention also relates to the use of diagnostic kits comprising a non-protein agent I producing aggregation of the circulating forms of the noninfectious proteins involved in pathological aggregation processes of the central nervous system and/or a non-protein agent II for capturing the natural aggregates of aggregate-forming circulating protein forms or the aggregates induced by said agents I, for detecting at least one aggregate-forming circulating protein form associated with noninfectious neurodegenerative diseases.

The method of the invention is therefore a method which is simple, universal in terms of application, and particularly useful for carrying out a diagnosis in biological samples, such as blood, of noninfectious neurodegenerative diseases, irrespective of the nature of the aggregate-forming circulating protein forms and of their concentration.

According to a first embodiment, it uses two agents, i.e.:

a non-protein agent I producing aggregation of the circulating forms of the noninfectious proteins involved in pathological aggregation processes of the central nervous system, and a non-protein agent II for capturing the natural aggregates of aggregate-forming circulating protein forms or the aggregates induced by said agents I.

The expression "nonprotein agent producing aggregation of the circulating forms of the noninfectious proteins involved in pathological aggregation processes of the central nervous system" is intended to mean any molecule of non-protein nature capable of bringing about, in its presence, the aggregation of aggregate-forming circulating protein forms, i.e. capable of producing protein masses of size greater than the initial aggregation-forming circulating protein forms and of allowing their rapid sedimentation by simple centrifugation. Aggregation is in fact defined as being the formation of multimolecular networks that can be sedimented by centrifugation at low speed (10 000 g).

The expression "non-protein agent for capturing the natural aggregates of aggregate-forming circulating protein forms or the aggregates induced by said agents I" is intended to mean any molecule of non-protein nature capable of binding to the aggregates of aggregate-forming circulating protein forms, irrespective of whether they are formed naturally, i.e. in the organism, or artificially, i.e. after reaction with the agents I.

The expression "neurodegenerative disease recognized as noninfectious to date" is intended to mean a disease characterized by extracellular and/or intracellular deposits of aggregate-forming circulating protein forms, as described above, these aggregate-forming circulating protein forms not being infectious proteins, i.e. transmissible proteins. Thus, prion diseases, such as Creutzfeldt-Jakob disease or bovine spongiform encephalopathy, are clearly excluded from this definition.

By way of examples of diseases included in the definition of the invention, mention may be made of Parkinson's disease, Alzheimer's disease, tauopathies, dementia with Lewy bodies, Huntington's disease and vascular dementia.

The biological samples in which the detection method of the invention is carried out are any sample of human origin that may contain at least one aggregate-forming circulating protein form.

By way of example of such samples, mention may be made of the brain, central nervous system tissues, organs such as the spleen and the intestine, and also biological is fluids such as cerebrospinal fluid, urine and blood, the latter being preferred, and blood constituting a biological sample of choice.

The non-protein agents I producing aggregation of the circulating forms of the noninfectious proteins involved in pathological aggregation processes of the central nervous system are all non-protein molecules having this aggregation function. These agents all have the particularity, unlike protein agents, of quantitatively and qualitatively amplifying the detection of the aggregate-forming circulating protein forms.

By way of example of an agent I, mention may be made of molecules having at least one positive charge. Positive charges provided by basic functions, such as guanidinium, pyridinium or ammonium functions, are preferred. The molecules having at least one positive charge that are preferred for the purposes of the invention are molecules having at least two guanidinium and/or pyridinium and/or ammonium functions, preferably in a nonpolymeric hydrophilic molecular system.

According to a specific embodiment of the invention, said agent I is a molecule having at least two guanidinium and/or pyridinium and/or ammonium functions.

Preferably, the molecules having at least two guanidinium and/or pyridinium and/or ammonium functions are chosen from aminoglycosides with a guanidinium nucleus, streptomycin being particularly preferred.

By way of example of an agent I, mention may also be made of the major antitubercular agents, such as rifampicin, isoniazide and ethambutol, this constituting a specific embodiment of the invention.

According to another specific embodiment of the invention, the agents I having at least two guanidinium and/or pyridinium and/or ammonium functions are chosen from triethylenetetraamine (TET), bis-3-aminopropyl amine, spermine tetrahydrochloride, dihydrostreptomycin sesquisulfate and streptomycin. Preferably, the agent I is chosen from streptomycin and TET.

Due to the specific characteristic of the agents I of allowing the aggregation of aggregate-forming circulating protein forms and of capturing them in an amplified manner in the sample to be tested, compared with protein agents such as antibodies (capture of more forms), it is possible to use only the agent I for detecting the aggregate-forming circulating protein forms.

Thus, the invention also relates to a method for detecting the aggregate-forming circulating protein forms associated with noninfectious neurodegenerative diseases, characterized in that it comprises or consists of the step of bringing a biological sample, derived or obtained from a human organism, together with a non-protein agent I producing aggregation of the circulating forms of the noninfectious proteins involved in pathological aggregation processes of the central nervous system, preferably a molecule having at least two guanidinium and/or pyridinium and/or ammonium functions.

Of course, the agents I are as defined above.

The non-protein agents II for capturing the natural aggregates of aggregate-forming circulating protein forms or aggregates induced by said agents I are all non-protein molecules having this capture function. By way of example of an agent II, mention may be made of macrocyclic molecules and glycosaminoglycans.

These agents all have the particularity, unlike protein agents, of quantitatively and qualitatively amplifying the detection of the aggregate-forming circulating protein forms.

According to one embodiment of the invention, the agent II is chosen from macrocyclic molecules and glycosaminoglycans.

Glycosaminoglycans are widely known to those skilled in the art and are described, for example, in Polysaccharides, M. Yalpani, Elsevier, Amsterdam, 1988.

By way of glycosaminoglycans suitable for the purposes of the invention, mention may, for example, be made of heparin, chondroitin sulfate, dermatan sulfate, hyaluronic acid and keratan sulfate.

The term "macrocyclic molecule" is intended to mean a compound consisting of a succession of rings forming a macrocycle.

Macrocyclic molecules are known to those skilled in the art. By way of nonlimiting examples, mention may be made of cyclophanes, metacyclophanes, cyclodextrins, cyclo(chromotropic tetraacid)s, spherands and cyclo[n]veratrylenes.

The macrocyclic molecules have the particular advantage that they make it possible to trap the protein to be tested, in free form or in aggregate form, via a cage effect.

The macrocyclic molecules can be prepared according to techniques known to those skilled in the art, for example described in Comprehensive Supramolecular Chemistry, Pergamon, Oxford, 1996.

The macrocyclic molecules that are preferred for the method of the invention are chosen from metacyclophanes, calixarenes being particularly preferred. Such calixarene compounds can be obtained according to the methodology described in Arduini, A. et al., 1996, Macrocycle Synthesis, Eds. Harwood, L. M. & Moddy, C. J. Oxford University Press, Oxford and Da Silva et al., 2001, J. Supramol. Chem., 1:135-138.

According to a preferred embodiment, the macrocyclic molecule of the invention corresponds to general formula (I) below:

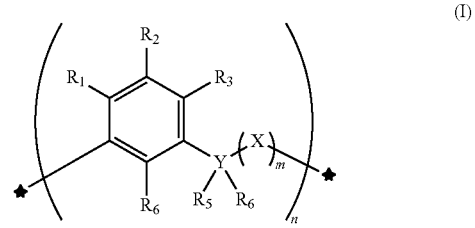

in which $R_1$ represents a hydrogen atom, a hydroxyl group, an OR group or an OCOR group, R being as defined below, $R_2$ represents a hydrogen atom, or an R, COR, Pol or $CH_2Pol$ group, in which Pol represents a phosphate, sulfate, amine, ammonium or carboxylic acid group and R is as defined below, $R_3$ represents a hydrogen atom, a hydroxyl group, an OR group or an OCOR group in which R is as defined below, $R_4$ represents a hydrogen atom, a hydroxyl group, an OR group, an $OCH_2R$ group or an OCOR group, in which R is as defined below, Y is a carbon, nitrogen or sulfur atom, $R_5$ and $R_6$, each independently, are absent or represent a hydrogen atom, or a $CH_2$ or R group as defined below, or else $R_5$ and $R_6$ together represent an oxygen or sulfur atom, X represents a $CH_2$ group or an oxygen or sulfur atom, m represents an integer equal to 0 or 1, R represents a hydrogen atom or a branched or unbranched, cyclic or noncyclic, saturated or unsaturated hydrocarbon-based chain which is unsubstituted or substituted with a halogen group, and which bears polar or nonpolar functions, n is an integer between 3 and 15, the substituents $R_1$ to $R_5$, R, X, Y and the integer m may be of different nature according to the units.

Thus, the compound of formula (I) is in the form of a succession of n units characterized by the presence of a benzene ring, and the substituents of this ring may be variable from one unit to the other, within the limit of their above definitions.

Of course, the presence of the stars in the formulae makes it possible to represent the necessary connection for the formation of a ring.

The branched or unbranched, cyclic or noncyclic, saturated or unsaturated hydrocarbon-based chains which are unsubstituted or substituted with a halogen group and which bear polar or nonpolar functions are widely known to those skilled in the art. By way of example, mention may be made of alkyls, alkenes, aryls and saturated rings such as cyclohexane. An example of a nonpolar group is $CF_3$ and examples of polar groups are the substituents Pol as defined above.

The compounds of formula (I) that are particularly preferred correspond to formula (Ia) below:

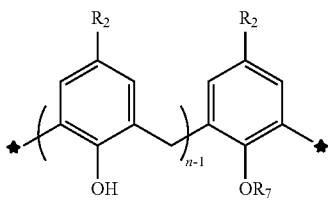

in which n is an integer between 4 and 8, each group $R_2$, taken independently, is a sulfate group or a phosphate group, $R_7$ represents a $(CH_2)_t$—$(CO)_s$—$(NH_2)$ group or a $(CH_2)_t$—COOH group where t is an integer between 0 and 6 and s is an integer between 0 and 6.

The compounds of formula (Ia) that are particularly preferred are those for which the two groups $R_2$ are each a sulfate group, n is 4, 6 or 8, and $R_7$ is a hydrogen atom, a —$CH_2COOH$ group, a —$CH_2CONH_2$ group or a —$CH_2CH_2NH_2$ group, this constituting an embodiment of the invention.

According to a preferred embodiment, the macrocyclic ligand corresponds to general formula (Ia) in which n=6, $R_2$=sulfate and $R_7$ is —$CH_2CH_2NH_2$.

Due to the specific characteristic of the agents II of allowing the capture of the aggregates of aggregate-forming circulating protein forms, in an amplified manner in the sample to be tested compared with protein agents such as antibodies (capture of more forms), it is possible to use only the agent II for detecting the aggregate-forming circulating protein forms.

Thus, the invention also relates to a method for detecting the aggregate-forming circulating protein forms associated with noninfectious neurodegenerative diseases, characterized in that it comprises or consists of the step of bringing a biological sample, derived or obtained from a human organism, together with a non-protein agent II for capturing the natural aggregates of aggregate-forming circulating protein forms, preferably a macrocyclic molecule or a glycosaminoglycan.

Of course, the agents II are as defined above.

The amount of agents I and II can be readily determined by those skilled in the art according to the specificities of the sample. Thus, for example, the amount of agent I, such as streptomycin, may be between 50 and 500 mg/ml, preferably between 100 and 300 mg/ml.

Against all expectations, the applicants have demonstrated that the aggregate-forming circulating protein forms to be detected in the method of the invention, for binding to the agents I, and in particular to the agents having at least two guanidinium and/or pyridinium and/or ammonium functions, contain amino acids whose side chains have either an acid function, preferably carboxylic acid function, such as aspartic acid (D) or glutamic acid (E), or a hydrogen-bond-acceptor function, such as serine (S) or asparagine (N), these amino acids (D, E, S or N) being present overall at least 4 times in a peptide sequence of length less than or equal to 20 amino acids. Preferably, a density of these amino acids (D, E, S or N) of greater than or equal to four over a peptide sequence of less than or equal to 20 amino acids is found at least twice over the complete sequence of the protein constituting the aggregate-forming circulating protein forms. Preferably, these amino acids (D, E, S or N) are present overall at least 5 times in a peptide sequence of length less than or equal to 20 amino acids or at least 4 times in a peptide sequence of length less than or equal to 16 amino acids. Preferably, a density as defined above is associated with an area of higher density for these amino acids (D, E, S or N), corresponding to at least 5 times in a peptide sequence of length less than or equal to 12 amino acids. A density of equivalent functions over an equivalent spatial distance can also constitute a structure that is a mimetic of that which was defined above in a primary protein structure.

Similarly, the applicants have demonstrated that, for binding to the agents II, and in particular to macrocyclic molecules such as calixarenes, the aggregate-forming circulating protein forms contain a minimum of three basic amino acids, preferably arginine (R), lysine (K), histidine (H) or glutamine (Q), in a peptide sequence of length less than or equal to twelve, or even fifteen, amino acids. A density of three equivalent positive charges, over an equivalent spatial distance, may also constitute a structure that is a mimetic of that which was defined above in a primary protein structure. This may, for example, be a conformation which projects these cations or their functional equivalents into a three-dimensional space equivalent to a sequence of twelve, or even fifteen, amino acids over a portion of this space representing an alpha-helix consisting of amino acids.

The addition of the two agents I and/or II to the biological sample in this method can be carried out in any order, since, against all expectations, this in no way impairs the detection of the aggregate-forming circulating protein forms, for example using a detection antibody against aggregate-forming circulating protein forms. However, it is preferred that said agent I be added to said biological sample for the aggregation of the aggregate-forming circulating protein forms before said agent II, this constituting an embodiment of the invention.

According to one embodiment of the invention, the method comprises or consists of the steps consisting in:
a) adding said agent I to said sample in order to aggregate the aggregate-forming circulating protein forms and precipitating them,
b) bringing the mixture thus obtained together with said agent II in order to capture said aggregates of aggregate-forming circulating protein forms, and
c) revealing the presence of the aggregate-forming circulating protein forms.

Preferably, in order to promote the precipitation the aggregate-forming circulating protein forms, after the addition of agent I, moderate heating of the reaction medium is carried out at a temperature of between 25 and 45° C., a temperature of 37° C. being preferred.

The aggregates of aggregate-forming circulating protein forms, formed in the presence of agent I, can be separated from the reaction medium before their reaction with agent II. The separation method can be carried out by any method of separating a precipitate known to those skilled in the art. By way of examples, the aggregates of aggregate-forming circulating protein forms are separated from the reaction medium by centrifugation or membrane separation, and then by elimination of the supernatant. This separation step makes it possible to remove all products not necessary for the subsequent reaction for detecting the aggregate-forming circulating protein forms, such as the agent I free in solution.

In order to promote, after formation of the aggregates with an agent I, the separation between the plasma ligands and the proteins, of the aggregate-forming circulating protein forms, to which said plasma ligands are bound (denaturation), a chemical denaturing agent such as guanidine-HCl can be added at the concentration of 1 to 6 mol/l and/or a heat denaturation can be carried out at 100° C., which makes it possible to free the masked epitopes of the proteins of the aggregate-forming circulating protein forms by separating them from the ligands which are not bound by agent I. This makes it possible to further enhance the sensitivity of the detection method of the invention. The denaturation of said aggregates present in the biological sample to be tested before the reaction of the aggregates of aggregate-forming circulating protein forms with agent II can also be carried out by any method for denaturing protein aggregates known to those skilled in the art.

Thus, the method for detecting aggregate-forming circulating protein forms according to the invention preferably comprises at least one of the following additional steps i) and ii) consisting in:
  i) separating the aggregates of aggregate-forming circulating protein forms from the reaction mixture, and
  ii) denaturing the aggregates of aggregate-forming circulating protein forms, these steps being included, where appropriate, between step a) and step b).

The visualization of the presence of the aggregate-forming circulating protein forms in a biological sample according to the method of the invention can be carried out according to the conventional methods for detecting analytes in a sample.

It can, for example, be carried out by an immunological or non-immunological detection.

The term "immunological detection" is intended to mean the demonstration of an immunoreaction with the aggregate-forming circulating protein forms, this immunoreaction consisting of binding between the aggregate-forming circulating protein forms to be detected and at least one binding partner specific for the aggregate-forming circulating protein forms, or else of a competition reaction between the aggregate-forming circulating protein forms that may be contained in the sample to be tested and labeled aggregate-forming circulating protein forms.

By way of non-immunological detection, mention may, for example, be made of the techniques for staining on an electrophoresis gel that are well known to those skilled in the art.

The detection of the aggregate-forming circulating protein forms by immunoreaction can be carried out, for example, after the addition of at least one binding partner specific for aggregate-forming circulating protein forms.

The expression "binding partner specific for the aggregate-forming circulating protein forms" is intended to mean any partner capable of binding to the aggregate-forming circulating protein forms in question. The visualization of the immunoreaction will then consist of the visualization of the binding partner specific for the aggregate-forming circulating protein forms/aggregate-forming circulating protein forms complex.

According to a preferred embodiment, the method of the invention is such that at least one binding partner specific for the aggregate-forming circulating protein forms is added for the immunoreaction between the binding partner specific for the aggregate-forming circulating protein forms and the aggregate-forming circulating protein forms, where appropriate in step c). Of course, such partners can also be added when it is decided to use only agent I or only agent II in the method of the invention.

The number of different binding partners to be added in the method of the invention depends on the number of different aggregate-forming circulating protein forms to be tested. Thus, in the case of the detection of Alzheimer's disease, if it is desired to test only the Tau protein, a Tau-specific binding partner will be added. On the other hand, if it is desired to detect both the Tau protein and beta-Amyloid peptides, binding partners specific for the beta-Amyloid peptides will also be added.

By way of binding partner specific for the aggregate-forming circulating protein forms, mention may, for example, be made of antibodies, antibody fragments, polypeptides, proteins, nucleic acids, haptens and aptamers.

The term "antibodies" includes polyclonal or monoclonal antibodies, antibodies obtained by genetic recombinations and antibody fragments.

The polyclonal antibodies can be obtained by immunization of an animal with at least one target antigen of interest, in the present case an aggregate-forming circulating protein form, followed by recovery of the desired antibodies in purified form, by taking a serum sample from said animal and separating said antibodies from the other serum constituents, in particular by affinity chromatography on a column to which is bound an antigen specifically recognized by the antibodies, in particular the aggregation-forming circulating protein form in question.

The monoclonal antibodies can be obtained by the hybridoma technique, the general principle of which is recalled hereinafter.

In a first step, an animal, generally a mouse (or cells in culture in the case of in vitro immunizations) is immunized with a target antigen of interest, in the present case an aggregate-forming circulating protein form, the B lymphocytes of said mouse then being capable of producing antibodies against said antigen. These antibody-producing lymphocytes are then fused with "immortal" myeloma cells (murine in the example) so as to give rise to hybridomas. The heterogeneous mixture of the cells thus obtained is then used as a source from which to select the cells capable of producing a specific antibody and of multiplying indefinitely. Each hybridoma is multiplied in the form of a clone, each resulting in the production of a monoclonal antibody whose recognition properties with respect to the antigen of interest may be tested, for example, by ELISA, by one- or two-dimensional immunoblotting, by immunofluorescence, or by means of a biosensor. The monoclonal antibodies thus selected are subsequently purified, in particular according to the affinity chromatography technique described above.

By way antibodies suitable for the invention, mention may, for example, be made of the monoclonal antibodies directed against the total Tau proteins (Tau-1 antibody (Chemicon), T46 (Zymed)), against the phosphorylated Tau protein (PHF-6 antibody (Zymed)), against the APP protein (22C11 antibody (Chemicon)), or against the beta-Amyloid peptides (6E10 and 4G8 antibodies (Sigma)).

The antibody fragments are such that they conserve the function of binding to the aggregate-forming circulating protein forms.

The term "polypeptide" is intended to a mean a sequence of at least two amino acids. The term "amino acids" is intended to mean primary amino acids which encode proteins, amino acids derived after enzymatic action, such as trans-4-hydroxyproline, and amino acids which are natural but not present in proteins, such as norvaline, N-methyl-L-leucine, staline (Hunt S. in Chemistry and Biochemistry of the amino acids, Barett G C, ed., Chapman and Hall, London, 1985), amino acids protected by chemical functions that can be used in solid-support or liquid-phase synthesis, and unnatural amino acids.

The term "protein" includes holoproteins and heteroproteins such as nucleoproteins, lipoproteins, phosphoproteins, metalloproteins and glycoproteins, both fibrous and globular.

The term "nucleic acid" is intended to mean oligonucleotides, deoxyribonucleic acids and ribonucleic acids, and derivatives thereof.

The term "oligonucleotide" denotes a sequence of at least 2 natural or modified nucleotides (deoxyribonucleotides or ribonucleotides, or both). The term "modified nucleotide" is intended to mean, for example, a nucleotide comprising a modified base and/or comprising a modification at the level of the internucleotide bond and/or at the level of the backbone. By way of example of a modified base, mention may be made of inosine, methyl-5-deoxycytidine, dimethylamino-5-deoxyuridine, diamino-2,6-purine and bromo-5-deoxyuridine. To illustrate a modified internucleotide bond, mention may be made of phosphorothioate, N-alkylphosphoramidate, alkyl phosphonate and alkyl phosphodiester bonds. Alpha-oligonucleotides such as those described in FR-A-2 607 507, LNAs such as phosphorothioate-LNA and 2'-thio-LNA described in Bioorganic & Medicinal Chemistry Letters, Volume 8, Issue 16, 18 Aug. 1998, pages 2219-2222, and the PNAs which are the subject of the article by M. Egholm et al., J. Am. Chem. Soc. (1992), 114, 1895-1897, are examples of oligonucleotides consisting of nucleotides, the backbone of which is modified.

The term "hapten" denotes nonimmunogenic compounds, i.e. compounds incapable by themselves of promoting an immune reaction by production of antibodies, but capable of being recognized by antibodies obtained by immunization of animals under known conditions, in particular by immunization with a hapten-protein conjugate. These compounds generally have a molecular mass of less than 3000 Da, and most commonly less than 2000 Da, and may, for example, be glycosylated peptides, metabolites, vitamins, hormones, prostaglandins, toxins or various medicaments, nucleosides and nucleotides.

Aptamers are capture partners of protein and nucleic nature, the function of which is to act as an antibody and to bind to protein ligands (Toulme, J. J. and Giege, R., 1998, Medecine Science, 14(2), 155-166).

These polypeptides, proteins, haptens and aptamers all have the ability to bind to the aggregate-forming circulating protein forms or to the aggregate of aggregate-forming circulating protein forms.

The visualization of the immunoreaction between the binding partner(s) specific for the aggregate-forming circulating protein forms and the aggregate-forming circulating protein forms used, in particular in step c), can be carried out by any detection means known to those skilled in the art, such as direct or indirect means.

In the case of direct detection, i.e. without the use of a label, the immunoreaction is observed, for example, by plasmon resonance or by cyclic voltametry on an electrode carrying a conductive polymer.

In the case of indirect detection, i.e. using a label, the labeling can be carried out by means of said binding partner specific for the aggregate-forming circulating protein forms, which will then be prelabeled.

The visualization of the presence of the aggregate-forming circulating protein forms in a biological sample according to the method of the invention can also be carried out according to a "competition" method. Prelabeled aggregate-forming circulating protein form is then added, in particular in step c), in place of the binding partner specific for aggregate-forming circulating protein forms. In this case, the detection signal is at a maximum in the absence of aggregate-forming circulating protein forms, and then gradually decreases as the concentration of aggregate-forming circulating protein form being sought, which is unlabeled, increases, due to the competition reaction.

The term "labeling" is intended to mean the attachment of a label capable of directly or indirectly generating a detectable signal. A nonlimiting list of these labels consists of:
  enzymes which produce a detectable signal, for example, by colorimetry, fluorescence or luminescence, such as horseradish peroxydase, alkaline phosphatase, α-galactosidase or glucose-6-phosphate dehydrogenase,
  chromophores such as luminescent or dye compounds,
  radioactive molecules such as $^{32}P$, $^{35}S$ or $^{125}I$,
  fluorescent molecules such as fluorescein, rhodamine, alexa or phycocyanins, and
  particles such as gold or magnetic latex particles, or liposomes.

Indirect systems can also be used, for instance by means of another ligand/antiligand couple. Ligand/antiligand couples are well known to those skilled in the art, and mention may, for example, be made of the following couples: biotin/streptavidin, hapten/antibody, antigen/antibody, peptide/antibody, sugar/lectin, polynucleotide/sequence complementary to the polynucleotide. In this case, it is the ligand which carries the binding agent. The antiligand can be detectable directly by the labels described in the previous paragraph, or it can itself be detectable by a ligand/antiligand.

These indirect detection systems can, under certain conditions, produce an amplification of the signal. This signal amplification technique is well known to those skilled in the art, and reference may be made to the article J. Histochem. Cytochem. 45: 481-491, 1997.

The labeling of proteins is widely known to those skilled in the art and is described, for example, by Greg T. Hermanson in Bioconjugate Techniques, 1996, Academic Press Inc, 525B Street, San Diego, Calif. 92101 USA.

According to the type of labeling used, for instance using an enzyme, those skilled in the art will add reagents for visualizing the labeling.

Such reagents are widely known to those skilled in the art and are described in particular in Principles and Practice of Immunoessay, 2$^{nd}$ Edition, Edited by C. Price, D. J. Newman Stockton Press, 1997, 345 Park Avenue South, New York.

The detection of aggregate-forming circulating protein forms may be a solid-phase detection, i.e. using a solid phase on which is fixed a capture partner intended to capture the protein to be detected. In the case of the present invention, it is the agent II which can serve as capture partner fixed beforehand on a solid support. An example of solid-phase detection well known to those skilled in the art is sandwich-type detection, such as ELISA-type detection.

Thus, according to a preferred embodiment of the invention, said agent II is bound to a solid support.

By way of solid support, mention may, for example, be made of beads, such as magnetic beads, and microtitration plates.

The agent II can be bound to the solid support in a manner known to those skilled in the art, such as by adsorption or covalent bonding, covalent bonding being preferred.

Thus, the solid support may be functionalized with a function capable of forming a bond with a function carried by said agent II. According to a preferred embodiment, the solid support is functionalized with an NHS(N-hydroxysuccinimide) bond or with an $NH_2$ function. This function can react with a function carried by the agent II. In this embodiment, the agents II carrying a function capable of reacting so as to form a bond with the functional bond of the solid support, in particular carrying an $NH_2$ or COOH bond, are particularly preferred.

For the implementation of the method for detecting at least one aggregate-forming circulating protein form of the invention, diagnostic kits comprising an agent I and an agent II may be used, said agents being as defined above.

Thus, the invention also relates to the use of a diagnostic kit comprising a non-protein agent I producing aggregation of the circulating forms of the noninfectious proteins involved in pathological aggregation processes of the central nervous system and/or a non-protein agent II for capturing the natural aggregates of aggregate-forming circulating protein forms, for detecting at least one aggregate-forming circulating protein form associated with noninfectious neurodegenerative diseases.

According to a preferred embodiment, said agent II present in the kit is bound to a solid support for carrying out the detection of at least one aggregate-forming circulating protein form according to a solid-phase detection method.

Figure 9:
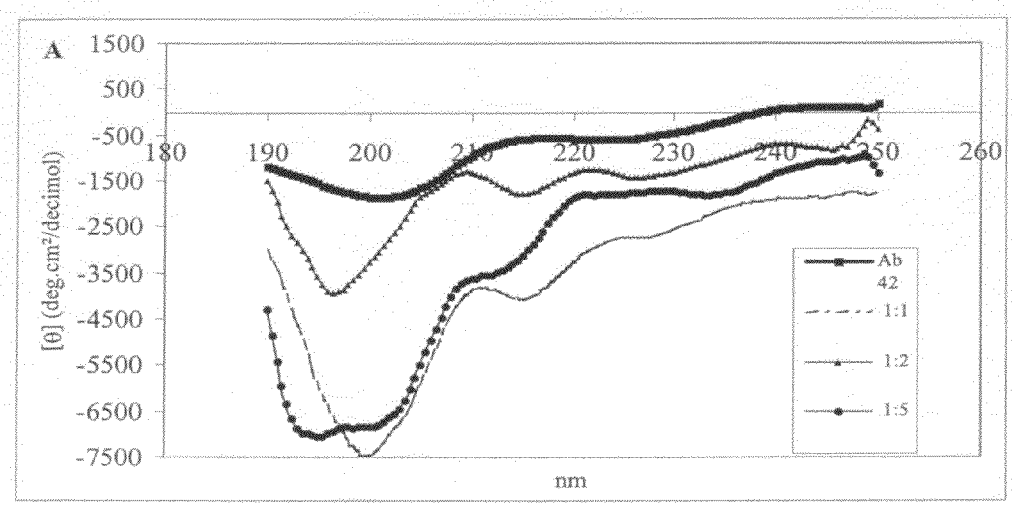
Figure 10:
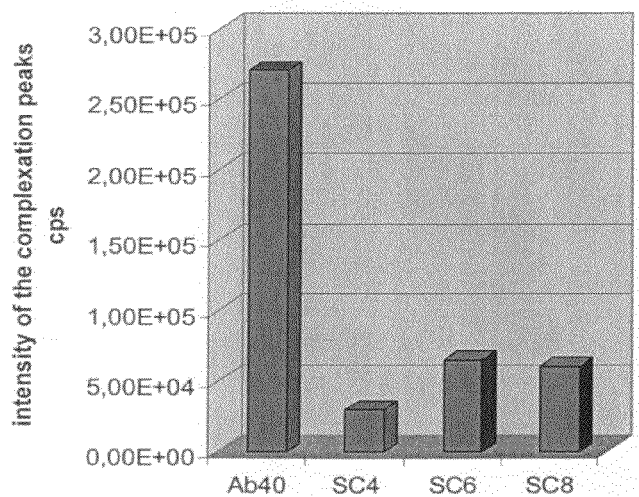
Figure 11:
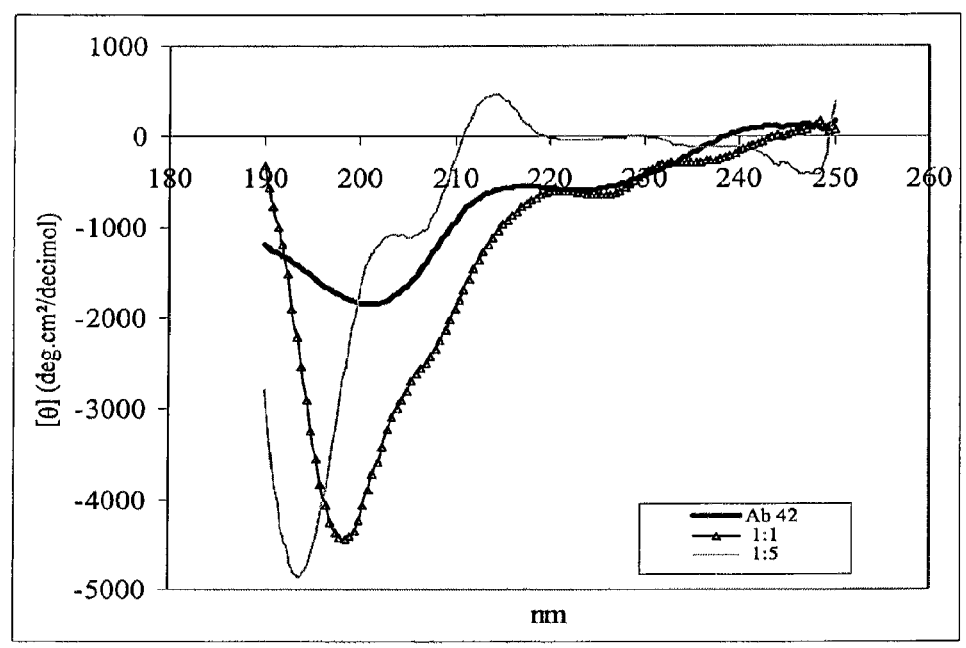
Figure 12:
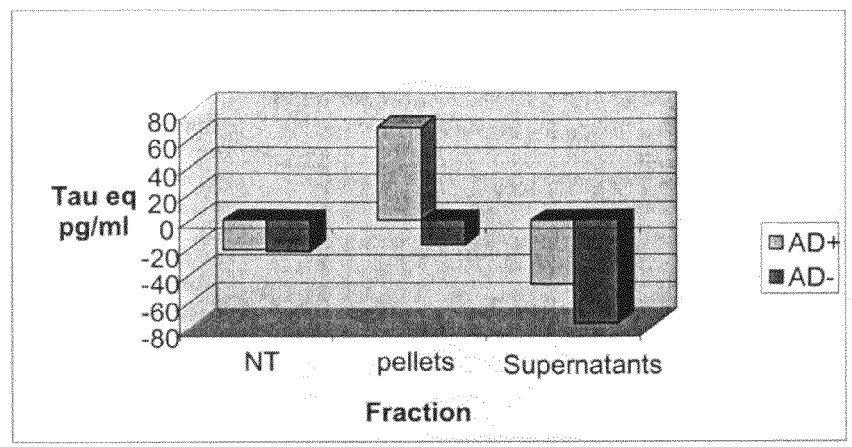
Figure 13:
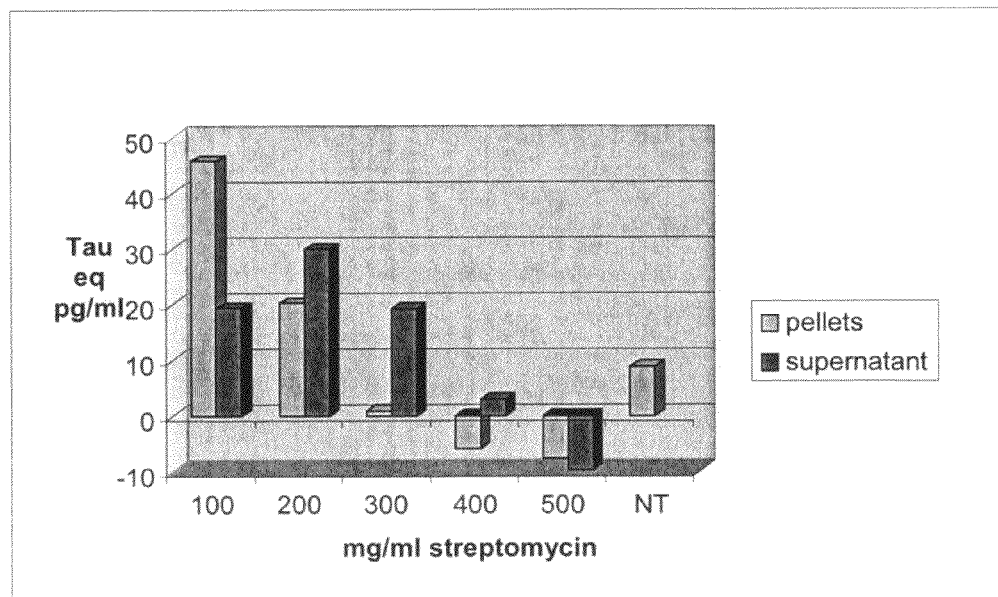
Figure 14:
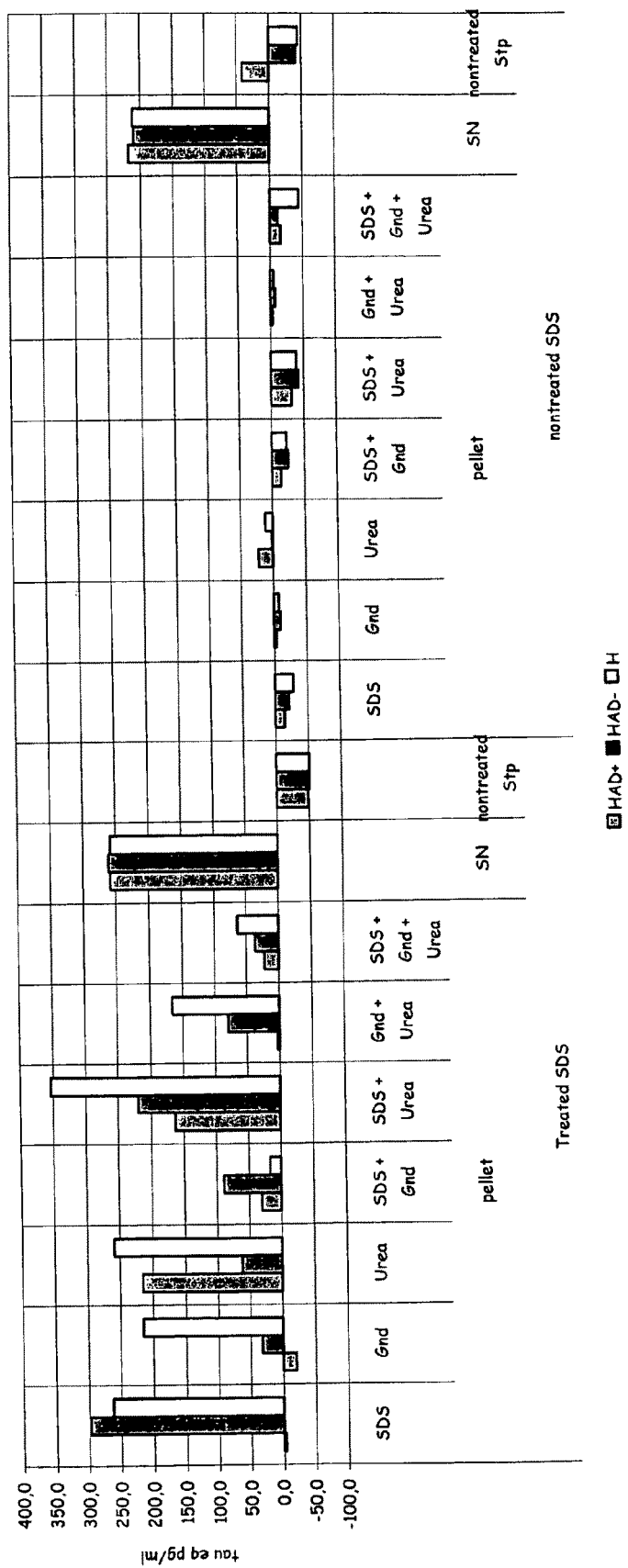
Figure 20:
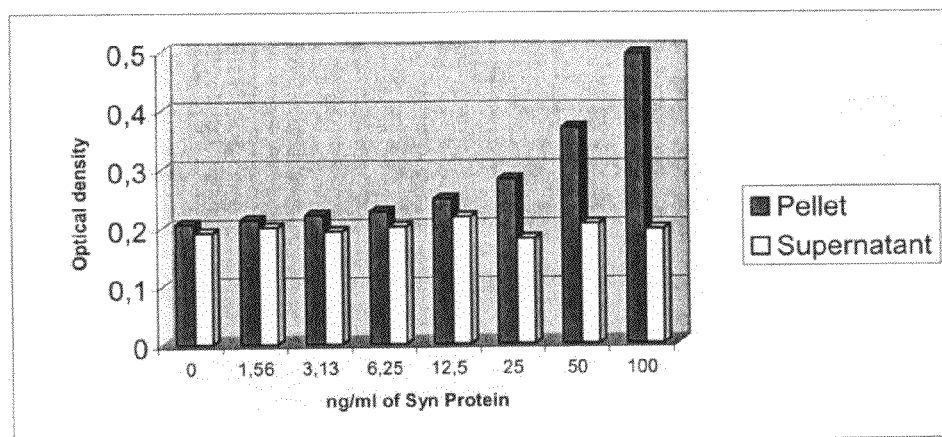
Figure 21:
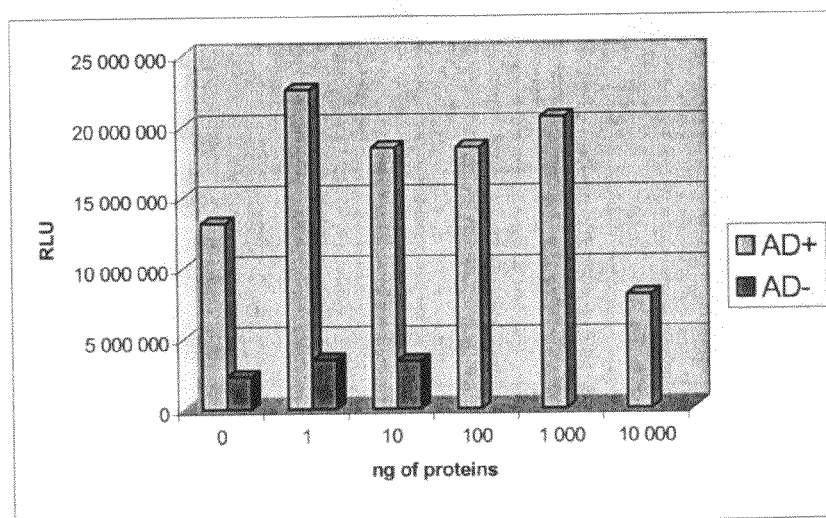
Figure 22:
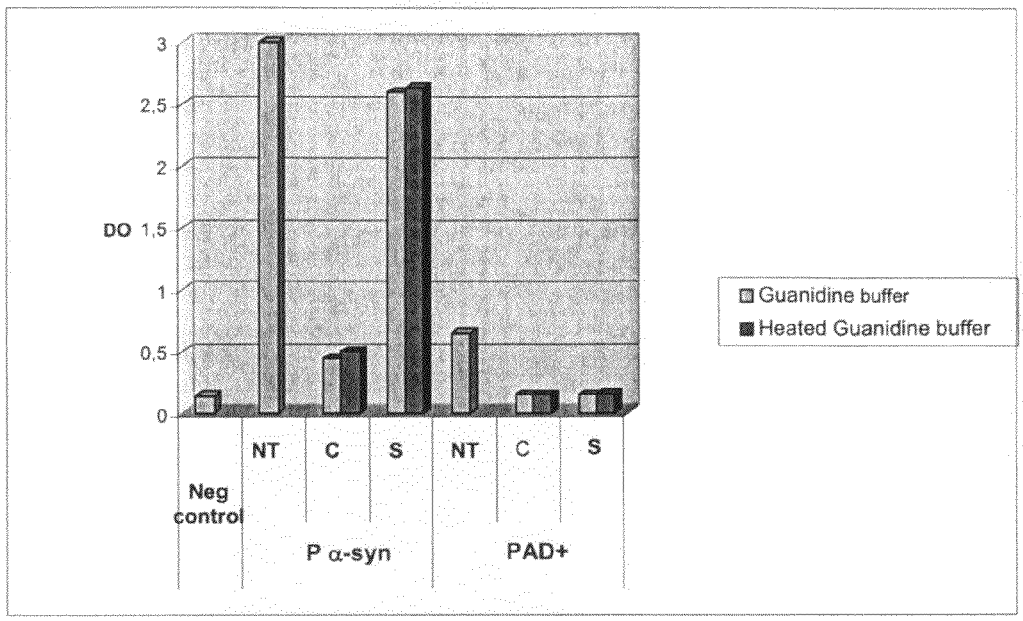
Figure 23:
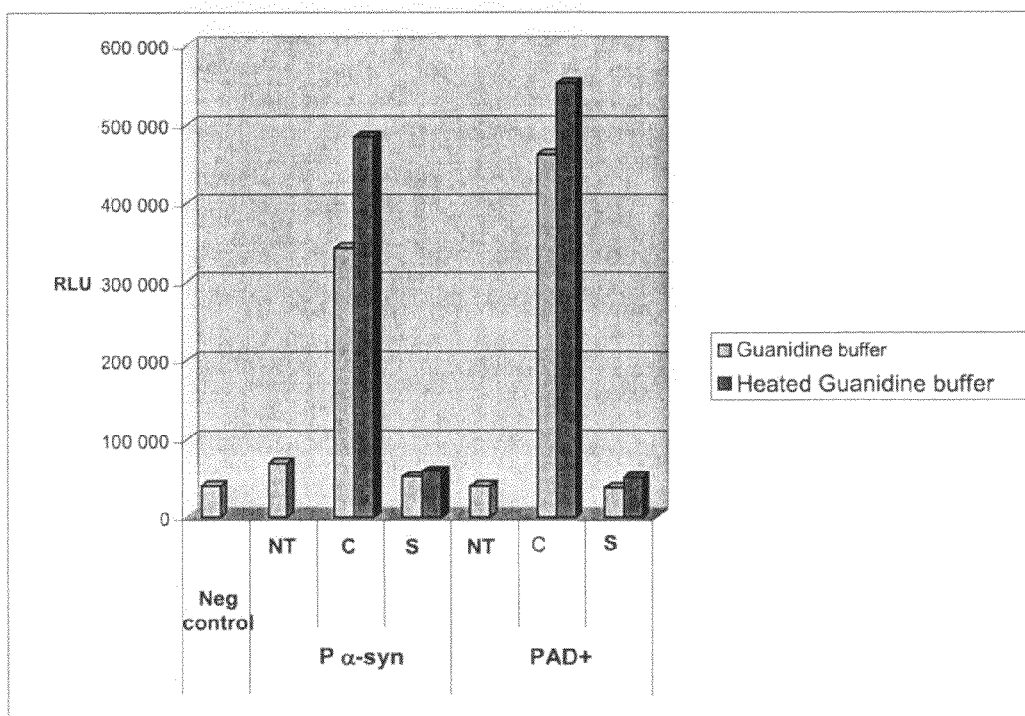
Figure 24:
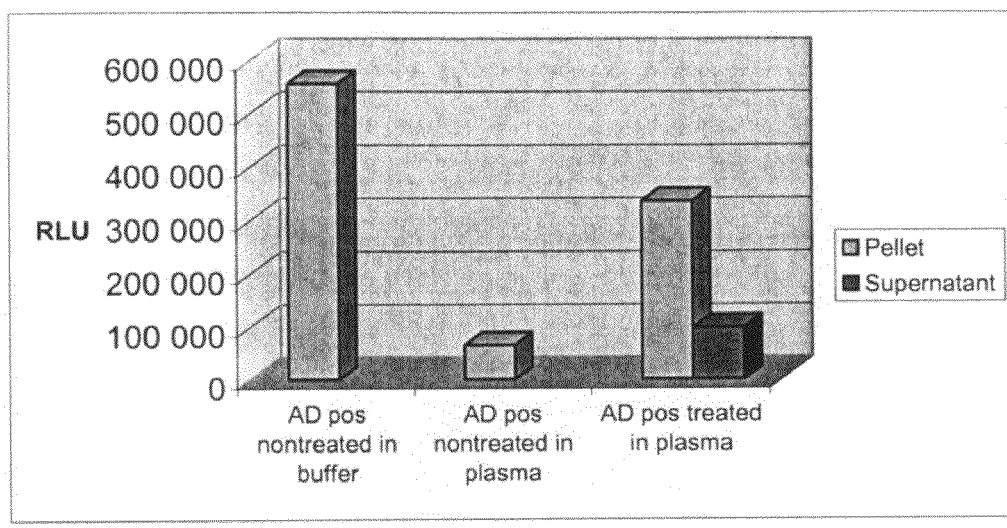

The invention will be understood more clearly from the following examples, given by way of nonlimiting illustration, and from the FIGS. 1 to 24, in which:

FIG. 1 shows a comparison of the sequences of the aggregate-forming circulating protein forms alpha-Synuclein, APP (Amyloid peptide precursor protein), Parkin and Tau protein;

FIG. 2 is a schematic representation (FIG. 2A) of the radiograph of an electrophoresis gel (FIG. 2B) following Western blotting, obtained after migration of the Tau protein treated with an agent I which is either streptomycin (lanes 3 and 4), or TET (lanes 5 and 6), lane 1 corresponding to the molecular weight marker lane and lane 2 corresponding to the control sample without treatment with agent I, FIG. 3 is a schematic representation (FIG. 3A) of the radiograph of an electrophoresis gel (FIG. 3B) following Western blotting, obtained after migration of the Tau protein treated with an agent I which is either rifampicin (lanes 3, 4 and 5) or isoniazide (lanes 8, 9 and 10), lanes 1 and 6 corresponding to the molecular weight marker lanes and lanes 2 and 7 corresponding to the control sample without treatment with agent I, FIG. 4 is a schematic representation (FIG. 4A) of the radiograph of an electrophoresis gel (FIG. 4B) following Western blotting, obtained after migration of the Tau protein treated with the calixarene p-sulfonato-3,7-(2-aminoethyloxy)-calix-[6]-arene (C6S) as agent II, the recovered fraction being either the pellet (lanes 2 to 9) or the supernatant (lanes 12 to 20), lanes 1 and 21 corresponding to the control sample without treatment with the calixarene, and lane 11 corresponding to the molecular weight marker lane, FIG. 5 is a schematic representation (FIG. 5A) of the radiograph of an electrophoresis gel (FIG. 5B) following Western blotting, obtained after migration of the beta-Amyloid peptide 1-40 treated with C6S (lane 2), with streptomycin (lane 3) or with TET (lane 4), lane 1 corresponding to the control sample without treatment with agent I or II, and lane 5 corresponding to the molecular weight marker lane, FIG. 6 is a schematic representation (FIG. 6A) of the radiograph of an electrophoresis gel (FIG. 6B) following Western blotting, obtained after migration of the beta-Amyloid peptide 1-40 treated with an agent I which is either rifampicin (lanes 3, 4 and 5) or isoniazide (lanes 8, 9 and 10), lanes 1 and 6 corresponding to the molecular weight marker lanes, and lanes 2 and 7 corresponding to the control sample without treatment with agent I, FIG. 7 is a schematic representation (FIG. 7A) of the radiograph of an electrophoresis gel (FIG. 7B) following Western blotting, obtained after migration of the beta-A peptide 1-42 treated with C6S (lane 2), with streptomycin (lane 3) or with TET (lane 4), lane 1 corresponding to the control sample without treatment with agent I or II, and lane 5 corresponding to the molecular weight marker lane, FIG. 8 is a schematic representation (FIG. 8A) of the radiograph of an electrophoresis gel (FIG. 8B) following Western blotting, obtained after migration of the beta-Amyloid peptide 1-42 treated with an agent I which is either rifampicin (lanes 3, 4 and 5) or isoniazide (lanes 8, 9 and 10), lanes 1 and 6 corresponding to the molecular weight marker lanes, and lanes 2 and 7 corresponding to the control sample without treatment with agent I, FIG. 9 is a graphic representation giving the molar ellipticity as a function of wavelength, obtained by circular dichroism of the beta-Amyloid peptide 1-42 after treatment with the agent II para-sulfonato-calix[4]arene according to various concentrations, Ab42 being the control without treatment with agent II, FIG. 10 is a graphic representation giving the intensity of the complexation peaks cps (counts per second) obtained by electrospray mode mass spectrometry of the beta-Amyloid peptide 1-40 after treatment with the agents II: para-sulfonato-calix[4]arene (SC4), para-sulfonato-calix[6]arene (SC6) and para-sulfonato-calix[8]arene (SC8), Ab40 being the control without treatment with agent II, FIG. 11 is a graphic representation giving the molar ellipticity as a function of wavelength, obtained by circular dichroism of the beta-amyloid peptide 1-42 after reaction with the agent II chondroitin-6-sulfate according to various concentrations, Ab42 being the control without treatment with agent II, FIG. 12 is a graphic representation of an ELISA assay carried out using extracts of brains from patients suffering from Alzheimer's disease (AD+) or not suffering from Alzheimer's diseases (AD−), not treated (NT) or treated with agent I, which is triethylenetetramine (TET). The detection of the phosphorylated Tau protein (in pg/ml, assayed in equivalents (eq) of recombinant Tau protein) is carried out in the pellet and supernatant fractions, FIG. 13 is a graphic representation of an ELISA assay carried out using extracts of brains of patients suffering from Alzheimer's disease, not treated (NT) or treated with various concentrations (mg/ml) of agent I, which is streptomycin. The detection of the phosphorylated Tau protein (eq Tau in pg/ml) is carried out in the pellet and supernatant fractions, FIG. 14 is a graphic representation showing the effect of various uptake buffers on the detection of the phosphorylated Tau protein, after no treatment or after treatment with 1% SDS and precipitation with streptomycin (500 mg/ml). The results were obtained using extracts of brains from patients suffering from Alzheimer's disease (PAD+) or not suffering from Alzheimer's disease (PAD−), or non-spiked plasma (P). Gnd: guanidine; SN: supernatant; stp: streptomycin, FIG. 15 is a schematic representation (top panel) of an electrophoresis gel (bottom panel) after staining with Coomassie blue (FIG. 15A) and of the radiograph of the same gel following Western blotting (FIG. 15B), obtained after migration of the SYN protein in plasma after treatment with TET (lanes 2-5: pellets; lanes 8-11: supernatants). Lanes 1 and 7 correspond to the pellets and supernatants of the control sample without the addition of agent I, lane 6 contains molecular weight markers (188, 62, 49, 38, 28, 18, 14, 6 and 3 kDa) and lane 12 corresponds to the recombinant protein alone, FIG. 16 is a schematic representation (top panel) of an electrophoresis gel (bottom panel) after staining with Coomassie blue (FIG. 16A) and of the radiograph of the same gel following Western blotting (FIG. 16B), obtained after migration of the SYN protein in plasma after treatment with streptomycin (lanes 2-5: pellets; lanes 8-11: supernatants). Lanes 1 and 7 correspond to the pellets and supernatants of the control sample without the addition of agent I, lane 6 contains molecular weight markers (188, 62, 49, 38, 28, 18, 14, 6 and 3 kDa), and lane 12 corresponds to the recombinant protein alone, FIG. 17 is a schematic representation (top panel) of an electrophoresis gel (bottom panel) after staining with Coomassie blue, obtained after migration of the SYN protein in plasma after treatment with calixarenes (agent II). FIG. 17A corresponds to the pellet fraction, while FIG. 17B corresponds to the supernatant fraction. Lanes 1 to 7 correspond to the Syn protein treated with various concentrations of calixarenes, lane 8 contains molecular weight markers (188, 62, 49, 38, 28 and 14 kDa), and lane 9 corresponds to the nontreated recombinant protein, FIG. 18 is a schematic representation (top panel) of the autoradiograph (bottom panel) of an electrophoresis gel following Western blotting, obtained after migration of the SYN protein in plasma after treatment the calixarenes (agent II). FIG. 18A corresponds to the pellet fraction, while FIG. 18B corresponds to the supernatant fraction. Lanes 1 to 7 correspond to the Syn protein treated with various concentrations of calixarenes, lane 8 contains molecular weight markers (188, 62, 49, 38, 28, 18, 14 and 6 kDa), and lane 9 corresponds to the nontreated recombinant protein, FIG. 19 is a schematic representation (top panel) of the autoradiograph (bottom panel) of an electrophoresis gel following Western blotting, obtained after migration of the SYN protein in plasma after treatment with the calixarenes (agent II). FIG. 19A corresponds to the pellet fraction, while FIG. 19B corresponds to the supernatant fraction. Lanes 1 to 8 correspond to various concentrations of the Syn protein treated with the calixarenes, lanes 10 to 12 correspond to the nontreated Syn protein, and lane 9 contains molecular weight markers (188, 62, 49, 38, 28, 18, 14 and 3 kDa), FIG. 20 is a graphic representation of an ELISA assay carried out using a range of concentrations (ng/ml) of Syn protein present in plasma, and treated with the calixarenes (agent II). The optical density is read in the pellet and supernatant fractions, FIG. 21 is a graphic representation of a sandwich-type ELISA assay in which the calixarenes (agent II) are used in the capture phase. Various amounts (ng) of proteins derived from extracts of brains from patients suffering from Alzheimer's disease (AD+) or not suffering from Alzheimer's disease (AD−) are tested. The results obtained are expressed in the form of a relative light unit (RLU), FIG. 22 is a graphic representation of a sandwich-type ELISA assay using a specific antibody in the capture phase. The assay is carried out using extracts of brains from patients suffering from Alzheimer's disease (PAD+) or using the recombinant alpha-synuclein protein (Pα-syn), spiked into a pool of human plasmas, and precipitated with an agent I, which is streptomycin. After precipitation, the pellets (C) are taken up in a heated or nonheated guanidine buffer. The results are expressed in the form of optical density. NT signifies not treated, C signifies pellet and S signifies supernatant, FIG. 23 is a graphic representation of a sandwich-type ELISA assay after precipitation with agent I (streptomycin) and detection by ELISA with capture using agent II (calixarene). The assay is carried out using extracts of brains from patients suffering from Alzheimer's disease (PAD+) or using the recombinant alpha-synuclein protein (Pα-syn), spiked into a pool of human plasmas. After precipitation with agent I, the pellets are taken up in a heated or nonheated guanidine buffer. The results are expressed in the form of optical density, FIG. 24 is a graphic representation of an ELISA assay of the phosphorylated Tau protein, carried out using an extract of a brain from a patient suffering from Alzheimer's disease (AD pos) spiked into a pool of plasmas from normal patients, not treated or treated with agent I, which is streptomycin. The capture phase consists of calixarenes (agent II). The results obtained in the pellet and supernatant fractions are expressed in the form of relative light units (RLU).

EXAMPLE 1

Compared Analysis of the Peptide Sequences of the Proteins Associated with Neurotoxic Aggregate Deposits in Noninfectious Neurodegenerative Diseases We used the "Mac Vector" software to carry out an alignment of the primary peptide sequences of proteins representative of the proteins associated with neurotoxic aggregate deposits in neurodegenerative diseases, i.e. the alpha-synuclein protein (SEQ ID No. 1), the amyloid precursor protein or APP (SEQ ID No. 2), the Parkin protein (SEQ ID No. 3) and the Tau protein (SEQ ID No. 4). The amino acids are numbered therein above the alignment, on the basis of their coincidence with the longest consensus sequence, and the dashes in the sequence for a protein represent a shift between its linear peptide sequence and the alignment of units common to all the proteins on the consensus sequence.

A "Clustal W" type alignment with a multiple alignment option was carried out and is shown in FIG. 1. The areas of homologies (amino acids which are identical or have equivalent chemical functionality) are boxed in and define domains common to these various proteins, one common property of which is that of forming neurotoxic aggregates in the central nervous system in neurodegenerative diseases.

The amino acids boxed in individually are representative of a more frequent repeat of certain amino acids of interest in the primary sequence of a protein in particular. These repeats may be distributed differently according to the proteins, but constitute a functional base that is more dense than the consensus, or else their projection in space can constitute a binding domain.

On the basis of our original knowledge regarding the functions involved in the binding with the agents I, such as organic compounds comprising at least two guanidinium and/or pyridinium and/or ammonium functions, or the agents II, such as calixarenes of calix-6-arene-sulfonate type, we were able to identify the amino acids bearing the functions described above with a particular density in these homologous regions.

It can thus be seen on FIG. 1 that, for binding to the agents I such as organic compounds comprising at least two guanidinium and/or pyridinium and/or ammonium functions, the regions as defined hereinafter contain a minimum of 4 amino acids chosen from D, E, S or N, in a peptide sequence of length less than or equal to 20 amino acids:
i) for alpha-Synuclein, for example, the regions
    124-143 have 4 residues D, E, S or N over 20 amino acids,
    231-261 have 10 residues D, E, S or N over 19 amino acids (the dashes indicate a shift in the numbering based on the consensus relative to the primary sequence, which means that the 20 amino acids are numbered over a number greater than their real number in the sequence range of the protein), and
    232-249 even have 6 residues D, E, S or N over 12 amino acids;
ii) for APP, for example, the regions
    80-98 have 5 residues D, E, S or N over 20 amino acids,
    193-216 have 14 residues D, E, S or N over 17 amino acids,
    225-236 have 6 residues D, E, S or N over 12 amino acids,
    247-256 have 9 residues D, E, S or N over 10 amino acids,
    692-702 have 5 residues D, E, S or N over 11 amino acids,
    713-718 have 4 residues D, E, S or N over 6 amino acids;
iii) for Parkin, for example, the regions
    25-46 have 8 residues D, E, S or N over 20 amino acids (due to the shifts in numbering with the consensus),
    153-172 have 8 residues D, E, S or N over 20 amino acids,
    224-240 have 5 residues D, E, S or N over 12 amino acids;
iv) for the Tau protein, the regions
    31-53 have 6 residues D, E, S or N over 20 amino acids,
    225-248 have 12 residues D, E, S or N over 20 amino acids,
    236-247 have 9 residues D, E, S or N over 12 amino acids,
    289-308 have 8 residues D, E, S or N over 20 amino acids,
    361-380 have 8 residues D, E, S or N over 20 amino acids,
    523-542 have 9 residues D, E, S or N over 20 amino acids, and
    753-764 have 5 residues D, E, S or N over 12 amino acids.

It may also be noted that a density of these amino acids (D, E, S or N) of greater than or equal to 4 over a peptide sequence of less than or equal to 20 amino acids can also be found at least twice on the complete sequence of the protein constituting the aggregate-forming circulating protein forms. Furthermore, it is noted that these amino acids (D, E, S or N) may be present overall at least 5 times in a peptide sequence of length less than or equal to 20 amino acids and/or at least 4 times in a peptide sequence of length less than or equal to 16 amino acids. Finally, a density as defined above may also be associated with an area of higher density for these amino acids (D, E, S or N), corresponding to at least 5 in a peptide sequence of length less than or equal to 12 amino acids. A density of equivalent functions over an equivalent spatial distance may also constitute a structure that is a mimetic of that which was defined above in a primary protein structure.

It is also interesting to note that the frequency of these amino acids can reach 32 out of 49 contiguous amino acids on the peptide sequence of APP, without however excluding other binding regions at a distance from this sequence of 49 residues (region 225-275).

Moreover, it may also be seen on FIG. 1 that, for binding to the agents II such as macrocyclic molecules of calixarene type, the regions as defined hereinafter contain a minimum of 3 basic amino acids—preferably arginine (R), lysine (K), histidine (H) or glutamine (Q)—in a peptide sequence of length less than or equal to twelve, or even fifteen, amino acids:
i) for alpha-Synuclein, the regions
    106-120 have 5 residues K, H, Q or R over 15 amino acids,
    128-142 have 4 residues K, H, Q or R over 15 amino acids,
    159-163 have 3 residues K, H, Q or R over 15 amino acids;
ii) for APP, the regions
    90-104 have 7 residues K, H, Q or R over 15 amino acids,
    105-116 have 4 residues K, H, Q or R over 12 amino acids,
    132-143 have 5 residues K, H, Q or R over 12 amino acids,
    153-163 have 3 residues K, H, Q or R over 12 amino acids,
    697-707 have 5 residues K, H, Q or R over 11 amino acids;
iii) for Parkin, the regions
    83-100 have 7 residues K, H, Q or R over 15 amino acids,
    182-195 have 6 residues K, H, Q or R over 12 amino acids;
iv) for the Tau protein, the regions
    101-108 have 4 residues K, H, Q or R over 8 amino acids,
    135-147 have 4 residues K, H, Q or R over 13 amino acids,
    178-183 have 3 residues K, H, Q or R over 6 amino acids,
    197-208 have 5 residues K, H, Q or R over 1 amino acid.

It may also be noted that a density of three equivalent positive charges, over an equivalent spatial distance, may also constitute a structure that is a mimetic of that which was defined above in a primary protein structure. This may be, for example, a conformation which projects these cations or their functional equivalents into a three-dimensional space equivalent to a sequence of twelve, or even fifteen amino acids over a portion of this space representing an alpha-helix consisting of amino acids.

EXAMPLE 2

Detection of the Tau Protein by Means of a Method Using an Agent I 2.1 Analytical Technique The analysis is carried out according to the Western blotting (Laemmli, UK 1970, Nature, 227: 680-685).

The samples to be analyzed are denatured in SDS buffer (125 mM Tris HCl, pH 6.8, 20% glycerol, 4% SDS, 0.02% bromophenol blue) (50/50 v/v) at 100° C. for 5 minutes. Said samples are then loaded onto a 12% polyacrylamide one-dimensional electrophoresis gel in the presence of sodium dodecyl sulfate (SDS-PAGE).

After migration, the proteins are transferred onto a nitrocellulose membrane and immunoblotted at 4° C. overnight with a monoclonal antibody specific for the Tau protein (Tau-1 antibody (Chemicon)).

The secondary detection antibody is a goat antibody which recognizes the heavy and light chains of mouse immunoglobulins G, conjugated to horseradish peroxidase.

The membrane is washed, between each step, in phosphate buffered saline (PBS) with and then without Tween 20 (0.05% w/v).

The signals are detected by chemiluminescence with the super signal kit (Pierce) and visualized on a radiographic film (Pierce).

2.2 Detection in the Presence of the Agent I

The assays are carried out with 1 µg of recombinant Tau protein fused to a tail of 6 histidines (Calbiochem) and with, as agent I, either streptomycin in sulfate form, or triethylenetetramine or TET, or rifampicin or isoniazide, with a ratio of amount of agent I (µg) to amount of total proteins (µg) equal to 9/1 or 35/1.

Once the recombinant protein and the agent I have been brought into contact, the mixture is incubated at 37° C. for 30 minutes.

The samples are then centrifuged for 10 minutes at 13 000 rpm. The pellets are recovered and, after denaturation, they are analyzed by the Western blotting technique.

The results are represented in FIGS. 2 and 3 as defined hereinafter:

FIG. 2 is a schematic representation (FIG. 2A) of the radiograph of an electrophoresis gel (FIG. 2B) of the Western blotting, obtained after migration of the Tau protein treated with streptomycin (lanes 3 and 4), or with TET (lanes 5 and 6), lane 1 corresponding to the molecular weight marker lane, and lane 2 corresponding to the control sample without treatment with agent I, and FIG. 3 is a schematic representation (FIG. 3A) of the radiograph of an electrophoresis gel (FIG. 3B) of the Western blotting, obtained after migration of the Tau protein treated with an agent I which is either rifampicin (lanes 3, 4 and 5), or isoniazide (lanes 8, 9 and 10), lanes 1 and 6 corresponding to the molecular weight marker lanes, and lanes 2 and 7 corresponding to the control sample without treatment with agent I.

The concentrations of agent I relative to the electrophoresis lanes are as indicated in Tables 1 and 2 below.

TABLE 1

| Lane | Sample loaded | Fraction |
|---|---|---|
| 1 | Molecular weight marker | no fractionation |
| 2 | Nontreated recombinant Tau, positive control for Western blotting | no fractionation |
| 3 | µg streptomycin/µg recombinant Tau: 9/1 | pellet |
| 4 | µg streptomycin/µg recombinant Tau: 35/1 | pellet |
| 5 | µg TET/µg recombinant Tau: 9/1 | pellet |
| 6 | µg TET/µg recombinant Tau: 35/1 | pellet |

TABLE 2

| Lane | Sample loaded | Fraction |
|---|---|---|
| 1 | Molecular weight marker | no fractionation |
| 2 | Nontreated recombinant Tau, positive control for Western blotting | no fractionation |
| 3 | µg rifampicin/µg recombinant Tau: 2/1 | pellet |
| 4 | µg rifampicin/µg recombinant Tau: 9/1 | pellet |
| 5 | µg rifampicin/µg recombinant Tau: 35/1 | pellet |
| 6 | Molecular weight marker | no fractionation |
| 7 | Nontreated recombinant Tau, positive control for Western blotting | no fractionation |
| 8 | µg isoniazide/µg recombinant Tau: 2/1 | pellet |
| 9 | µg isoniazide/µg recombinant Tau: 9/1 | pellet |
| 10 | µg isoniazide/µg recombinant Tau: 35/1 | pellet |

The results show that the Tau protein and its digested forms are found in the pellet after treatment with the agent I, irrespective of whether it is streptomycin, TET, rifampicin or isoniazide. Their presence in the sedimentation pellet attests to the fact that they have been concentrated from the volume of sample tested, which does not occur in the absence of agent I. These molecules therefore induce precipitation of the Tau protein after incubation for 30 minutes at 37° C. and simple centrifugation.

EXAMPLE 3

Detection of the Tau Protein by Means of a Method Using an Agent II 3.1 Analytical Technique It is identical to that described in point 2.1 above.

3.2 Detection carried out in the presence of the calixarene p-sulfonato-3,7-(2-aminoethyloxy)calix-[6]-arene (referred to as C6S) as agent II The assays are carried out as indicated in point 2.2 above, apart from the fact that C6S prepared as indicated patent application WO2004/059322 is used, with a concentration range of from 0.5 mM to 60 mM.

The results are given in FIG. 4, which is a schematic representation (FIG. 4A) of the radiograph of an electrophoresis gel (FIG. 4B) of the Western blotting, obtained after migration of the Tau protein treated with the calixarene p-sulfonato-3,7-(2-aminoethyloxy)calix-[6]-arene as agent II, the recovered fraction being either the pellet (lanes 2 to 9), or the supernatant (lanes 12 to 20), lanes 1 and 21 corresponding to the control sample without treatment with the calixarene, and lane 11 corresponding to the molecular weight marker lane.

The concentrations of agent II relative to the electrophoresis lanes are as indicated in Table 3 below.

TABLE 3

| Lane | Sample loaded | Fraction |
|---|---|---|
| 1 | Nontreated recombinant Tau, positive control for Western blotting | no fractionation |
| 2 | Recombinant Tau + 0.5 mM final of C6S | pellet |
| 3 | Recombinant Tau + 2.5 mM final of C6S | pellet |
| 4 | Recombinant Tau + 5 mM final of C6S | pellet |
| 5 | Recombinant Tau + 10 mM final of C6S | pellet |
| 6 | Recombinant Tau + 20 mM final of C6S | pellet |
| 7 | Recombinant Tau + 30 mM final of C6S | pellet |
| 8 | Recombinant Tau + 40 mM final of C6S | pellet |
| 9 | Recombinant Tau + 50 mM final of C6S | pellet |
| 10 | Recombinant Tau with 60 mM final of C6S | pellet |
| 11 | Molecular weight marker | no fractionation |
| 12 | Recombinant Tau + 60 mM final of C6S | supernatant |
| 13 | Recombinant Tau + 50 mM final of C6S | supernatant |
| 14 | Recombinant Tau + 40 mM final of C6S | supernatant |
| 15 | Recombinant Tau + 30 mM final of C6S | supernatant |
| 16 | Recombinant Tau + 20 mM final of C6S | supernatant |
| 17 | Recombinant Tau + 10 mM final of C6S | supernatant |
| 18 | Recombinant Tau + 5 mM final of C6S | supernatant |
| 19 | Recombinant Tau + 2.5 mM final of C6S | supernatant |
| 20 | Recombinant Tau + 0.5 mM final of C6S | supernatant |
| 21 | Nontreated recombinant Tau, positive control for Western blotting | no fractionation |

These results show that the Tau protein and its digested forms are found in the pellet after treatment with C6S and that, in the absence of agent II, no concentration or separation of the Tau protein is observed. These molecules therefore induce capture of the Tau protein after incubation for 30 minutes at 37° C. and sediment said protein via simple centrifugation. Furthermore, optimum precipitation is observed at from 0.5 mM to 40 mM.

EXAMPLE 4

Detection of Beta-Amyloid Peptides by Means of a Method Using an Agent I or an Agent II The protocol indicated in Examples 2 and 3 above is repeated, except for the fact that the following are used:

10 μg of synthetic beta-amyloid peptide 40 amino acids in length (beta-A peptide 1-40; SEQ ID No. 5) or 10 μg of synthetic beta-amyloid peptide 42 amino acids in length (beta-A peptide 1-42; SEQ ID No. 6), a monoclonal antibody specific for amyloid peptides (6E10 antibody (Sigma)), as agent I, streptomycin and TET, with a ratio of the amount of agent I (μg) to the amount of total proteins (μg) equal to 35/1, or else rifampicin and isoniazide, with a ratio of the amount of agent I (μg) to the amount of total proteins (μg) equal to 2/1, 9/1 or 35/1, and as agent II, C6S at a final concentration of 1 mM.

The Western blotting is carried out with the centrifugation pellets, which were analyzed as described in Example 2.

The results are given in FIGS. 5 to 8 as defined hereinafter:

FIG. 5 is a schematic representation (FIG. 5A) of the radiograph of an electrophoresis gel (FIG. 5B) of the Western blotting, obtained after migration of the beta-amyloid peptide 1-40 treated with C6S (lane 2), with streptomycin (lane 3) or with TET (lane 4), lane 1 corresponding to the control sample without treatment with agent I or II, and lane 5 corresponding to the molecular weight marker lane, FIG. 6 is a schematic representation (FIG. 6A) of the radiograph of an electrophoresis gel (FIG. 6B) of the Western blotting, obtained after migration of the beta-amyloid peptide 1-40 treated with an agent I, which is either rifampicin (lanes 3, 4 and 5), or isoniazide (lanes 8, 9 and 10), lanes 1 and 6 corresponding to the molecular weight marker lanes, and lanes 2 and 7 corresponding to the control sample without treatment with agent I, FIG. 7 is a schematic representation (FIG. 7A) of the radiograph of an electrophoresis gel (FIG. 7B) of the Western blotting, obtained after migration of the beta-amyloid peptide 1-42 treated with C6S (lane 2), with streptomycin (lane 3) or with TET (lane 4), lane 1 corresponding to the control sample without treatment with agent I or II, and lane 5 corresponding to the molecular weight marker lane, FIG. 8 is a schematic representation (FIG. 8A) of the radiograph of an electrophoresis gel (FIG. 8B) of the Western blotting, obtained after migration of the beta-amyloid peptide 1-42 treated with an agent I, which is either rifampicin (lanes 3, 4 and 5), or isoniazide (lanes 8, 9 and 10), lanes 1 and 6 corresponding to the molecular weight marker lanes, and lanes 2 and 7 corresponding to the control sample without treatment with agent I.

The concentrations of agent I or II relative to the electrophoresis lanes are as indicated in Tables 4 and 5 below, corresponding to FIGS. 5 and 7 (Table 4) and to FIGS. 6 and 8 (Table 5).

TABLE 4

| Lane | Sample loaded | Fraction |
| --- | --- | --- |
| 1 | Nontreated peptide, positive control for Western blotting | no fractionation |
| 2 | Treated peptide + 1 mM final of C6 monoacid | pellet |
| 3 | μg streptomycin/μg peptide: 35/1 | pellet |
| 4 | μg TET/μg peptide: 35/1 | pellet |
| 5 | Molecular weight marker | no fractionation |

TABLE 5

| Lane | Sample loaded | Fraction |
| --- | --- | --- |
| 1 | Molecular weight marker | no fractionation |
| 2 | Nontreated peptide, positive control for Western blotting | no fractionation |
| 3 | μg rifampicin/μg peptide: 2/1 | pellet |
| 4 | μg rifampicin/μg peptide: 9/1 | pellet |
| 5 | μg rifampicin/μg peptide: 35/1 | pellet |
| 6 | Molecular weight marker | no fractionation |
| 7 | Nontreated peptide, positive control for Western blotting | no fractionation |
| 8 | μg isoniazide/μg peptide: 2/1 | pellet |
| 9 | μg isoniazide/μg peptide: 9/1 | pellet |
| 10 | μg isoniazide/μg peptide: 35/1 | pellet |

As previously, the results show that the beta-amyloid peptides and their oligomers are found in the pellet after treatment with agent I or agent II. These molecules therefore induce precipitation of the peptides after incubation for 30 minutes at 37° C. and a simple centrifugation.

Furthermore, as shown in FIG. 7, lane 1, the high-molecular-weight oligomers (multimers), not normally captured by protein agents such as antibodies that are conventionally used, are captured and precipitated with the agent II, which prove their effectiveness on these multimerized forms. The agent II thus makes it possible to recover both the monomeric forms and the oligomeric forms without crosslinking them (various bands observed in electrophoretic migration).

Similarly, as shown in FIG. 8, lane 5, the high-molecular-weight oligomers (multimers), not usually crosslinked with protein agents such as antibodies that are conventionally used, are crosslinked and precipitated with the agent I, which proves their effectiveness on these multimerized forms. Moreover, the agent I also makes it possible to crosslink all the monomeric and oligomeric forms, which is demonstrated by the electrophoretic migration of all the antigenic beta-amyloid fractions in a relatively homogeneous region ("smear") of high molecular weight.

EXAMPLE 5

Interaction of the Beta-Amyloid Peptide 1-42 with para-sulfonato-calix[4]arene 5.1. Analytical Technique The analysis is carried out by circular dichroism.

The beta-amyloid peptide to be analyzed as defined above, also called $A\beta_{42}$, is extemporaneously dissolved at a stock concentration of $2.2 \times 10^{-4}$ M in a solution of trifluoroethanol (TFE) at 20% in water in order to structure the β-amyloid peptides. The para-sulfonato-calix[n]arenes, prepared as described in Da Silva, E. et al., 2003, Tetrahedron, 59(37): 7357-7364, are dissolved at 100 μM in 50 mM phosphate buffer. The samples are prepared so as to be able to obtain a final concentration of 10 μM of beta-amyloid peptide in a phosphate buffer, i.e. for a final volume of 500 μL. The peptide concentration/calixarene concentration ratios can vary from 1/0 to 1/5.

A β-amyloid control without para-sulfonato-calix[n]arene is carried out: 22.5 μL of $A\beta_{42}$ stock solution at $2.2 \times 10^{-4}$ M (5 nmol) in 20% TFE, 477.5 μL of 50 mM phosphate buffer.

The samples are analyzed by circular dichroism between 180 and 260 nm.

5.2. Interaction of the $A\beta_{42}$ Peptide with para-sulfonato-calix[4]arene

The assays are carried out for $A\beta_{42}$ peptide/calixarene concentration ratios of 1/1, 1/2 and 1/5, as indicated in Table 6 below. The control is a sample of $A\beta_{42}$ peptide without calixarene (1/0). The solutions are prepared for a final volume of 500 μL. The Aβ$_{42}$ peptide has a molar mass of 4514 g/mol, the para-sulfonato-calix[4]arene has a molar mass of 744 g/mol.

TABLE 6

| Concentration ratio | Constituents | | | |
| --- | --- | --- | --- | --- |
| | Aβ$_{42}$ peptide solution | Calixarene solution | 50 mM phosphate buffer | Final volume |
| 1/0 | 22.5 μL | 0 μL | 477.5 μL | 500 μL |
| 1/1 | 22.5 μL | 50 μL | 427.5 μL | 500 μL |
| 1/2 | 22.5 μL | 100 μL | 377.5 μL | 500 μL |
| 1/5 | 22.5 μL | 250 μL | 227.5 μL | 500 μL |

The results are shown in FIG. 9, which is a graph giving the molar ellipticity as a function of wavelength, the results being obtained for the control without calixarene (Ab42) and for the concentration ratios 1/1, 1/2, 1/5.

The curves in FIG. 9 demonstrate that the peptide, which is initially in the form of an α-helix, adopts, in the presence of the para-sulfonato-calix[4]arene, the three structures α-helix (210 nm), β-sheet (220 nm) aperiodic structure (200 nm), irrespective of the concentration of calix[4]arene used, either at low concentration (1/1) or at high concentration (1/5). The α-helix structure represents more than 37% of the visible structures, the β-sheets more than 26% and, finally, the aperiodic structure is present at 38%.

We observe that, at the 1/1 concentration ratio, the molar ellipticity of the structures increases compared with at 1/2. On the other hand, the spectrum for the concentration in the 1/5 ratio for the Aβ$_{42}$ peptide is close to that for 1/1 around the wavelengths in the region of 210 nm, and is close to 1/2 beyond this.

These variations demonstrate the molecular interaction between the agent II and the beta-amyloid peptide by virtue of the significant structural modifications observed on the spectrum.

EXAMPLE 6

Study of Complexation of the β-amyloid Peptide 1-40 with the para-sulfonato-calix[n]arenes by Electrospray Mode Mass Spectrometry 6.1. Analytical Technique The ●-amyloid peptide (also called Aβ$_{40}$) and the various para-sulfonato-calix[n]arenes (n=4, 6, 8), prepared as described by Da Silva, E. et al., 2003, above, are solubilized at a concentration of 100 μM in 10 mM ammonium acetate buffer. The solution of ●-amyloid peptide to be tested is mixed extemporaneously with the solution of para-sulfonato-calix[n]arenes. The samples are injected directly into electrospray mode mass spectrometry.

6.2. Study of Complexation of the A●$_{40}$ Peptide with the Various para-sulfonato-calix[n]arenes A 10 μM stock solution of A●$_{40}$ peptide (Mw=4430 g/mol) in a 10 mM ammonium acetate buffer is prepared. The various para-sulfonato-calix[n]arenes (n=4:SC4 Mw=744 g/mol; n=6:SC6 Mw=1116 g/mol; n=8:SC8 Mw=1488 g/mol) are solubilized at 100 μM in a 10 mM ammonium acetate buffer.

100 μL of the 100 μM A●$_{40}$ peptide solution are mixed with 100 μL of a 100 μM solution of para-sulfonato-calix[n]arene. The samples are injected extemporaneously into electrospray mode mass spectrometry.

The results obtained are shown in FIG. 10, which is a graphic representation giving the intensity of the complexation peaks cps (counts per second), obtained by electrospray mode mass spectrometry of the beta-amyloid peptide 1-40 after reaction with the agents II: para-sulfonato-calix[4]arene (SC4), para-sulfonato-calix[6]arene (SC6), para-sulfonato-calix[8]arene (SC8), Ab40 being the control without treatment with agent II.

These results show peaks characteristic of the complexation of the para-sulfonato-calix[n]arenes with the Aβ$_{40}$ peptide. It may be noted that the control is present in too great an excess, which explains the peak.

EXAMPLE 7

Interaction of the Beta-Amyloid Peptide 1-42 with chondroitin-6-sulfate

The protocol described in Example 5 above was repeated, with the exception that chondroitin-6-sulfate (Sigma) was used as agent II.

The results are given in FIG. 11, which is a graphic representation giving the molar ellipticity as a function of wavelength for the control without calixarene (Ab42) and for the concentration ratios 1/1 and 1/5.

The results obtained in FIG. 11 show that the Aβ$_{42}$ spectrum exhibits two negative minima, the first at 201 nm and the second at 226 nm. This synthetic β-amyloid peptide adopts an α-helical structure with a part being in the form of an aperiodic structure.

In the presence of chondroitin-6-sulfate, at a concentration equal to that of Aβ$_{42}$, the structure of the peptide changes. Three structures are present at similar percentages. Specifically, the α-helix (at 210 nm) is present at more than 37%, the aperiodic structure (at 200 nm) is greater than 26%. Finally, the β-sheet appears at 220 nm.

When the concentration of chondroitin-6-sulfate is increased to five times greater than that of the Aβ$_{42}$ peptide, the secondary conformation of the latter changes and adopts an essentially aperiodic structure.

In conclusion, in the presence of chondroitin-6-sulfate at concentration equal to that of the amyloid peptide, β-sheets appear, whereas, at a high concentration of chondroitin-6-sulfate, this conformation is replaced with an aperiodic structure.

These variations demonstrate the molecular interaction between the agent II and the beta-amyloid peptide by virtue of the significant structural modifications observed on the spectrum.

EXAMPLE 8

Detection of the Phosphorylated Tau Protein by Means of a Method using a Precipitating Agent I 8.1 Analytical Technique The analysis is carried out according to the conventional "ELISA sandwich-type" immunoenzymatic technique as described by Kohnken et al. (Neuroscience Letters 287 (2000) 187-190).

The PhosphoTau Elisa assay is based on the use of Dynex microplates to which are bound 3 μg/ml of goat anti-mouse Fc antibodies (Pierce) in a 25 mM KHPO$_4$ buffer (pH 7.2) containing 140 mM NaCl, 1 mM EDTA and 2 mM NaN$_3$, for three hours at 24° C. The wells are then passivated with a TBS (25 mM Tris-HCl, pH 7.5, 140 mM NaCl)-casein (1%) buffer for 1 h at 24° C., and then incubated for 2 h at 24° C. with 3 μg/ml of Tau1 (Chemicon) and CP27 (AppliedNeuroSolutions) antibodies diluted in TBS casein buffer.

Standards and brain extracts are diluted in a pool of normal plasmas for these assays and deposited at a rate of 80 µL per well in duplicate. The detection antibody CP9 (Applied-NeuroSolutions, US) is diluted in a buffer containing 200 µg/ml of human albumin, 22 µg/ml of human IgG and 0.15 µg/ml of human IgM, in a Krebs-Ringer bicarbonate buffer. 20 µl of this mixture are added to each well and incubated for 66 hours at 24° C. To recognize the bound CP9 antibody, a biotinylated anti-mouse IgM goat antibody (F(ab')$_2$) (Accurate) at 0.2 µg/ml in TBS-casein buffer containing 1% of normal human serum (Biocell) is added for 2 h at 24° C. The biotinylated antibody is detected with 0.4 µg/ml of a streptavidin-peroxydase conjugate (Pierce) diluted in TBS-casein buffer and incubated for 45 minutes at 24° C. A Lumiglo reagent (Kirkegaard and Perry laboratories, US) is added to each well and the chemiluminescence is read in a luminometer (Berthold, Centro LB 960). The data obtained are in the form of relative light units (RLU), the concentrations in pg/ml, assayed in recombinant tau equivalents, being generated by relating the RLU of the samples to the standard curve (RLU as a function of the concentration in pg/ml). Between each step described above, the wells are washed with TBS buffer containing 0.1% of Tween20.

8.2 Detection in the Presence of the Agent I, TET

The assays are carried out with 25 ng of brain extracts and with, as agent I, triethylenetetramine, or TET, at 100 mg/ml.

Once the sample and the agent I have been brought into contact, the mixture is incubated for 60 minutes at 37° C.

The samples are then centrifuged for 10 minutes at 13 000 rpm. The pellets are recovered and are separated from the supernatants. All the fractions are conserved. The pellets are taken up with 250 µl of tris-maleate buffer (unless otherwise indicated). The samples are then ready to be deposited on plates.

FIG. 12 summarizes the results obtained on extracts of brains from Alzheimer (AD+) or non-Alzheimer (AD−) patients, spiked into plasma. The results were generated in the absence of (NT) or after treatment with TET at 100 mg/ml and analysis of the two pellet and supernatant fractions.

The results show that the phosphorylated Tau protein is found in the pellet after treatment with the agent I, TET. Its presence in the sedimentation pellet attests to the fact that it has been concentrated by aggregation from the volume of sample tested, which does not occur in the absence of agent I. These molecules therefore induce precipitation of the recombinant Tau protein after incubation for 60 minutes at 37° C. and a simple centrifugation; the protein is then available for detection by means of an ELISA technique that can be used routinely in a clinical laboratory.

8.3 Detection in the Presence of the agent I, streptomycin

The assays are carried out with 25 ng of brain extracts and with, as agent I, streptomycin, in sulfate form, at various concentrations.

Once the sample and the agent I have been brought into contact, the mixture is incubated for 60 minutes at 37° C.

The samples are then centrifuged for 10 minutes at 13 000 rpm. The pellets are recovered and are separated from the supernatants. All the fractions are conserved. The pellets are taken up with 250 µl of tris-maleate buffer (unless otherwise indicated). The samples are then ready to be deposited onto plates.

FIG. 13 summarizes the results obtained on extracts of brains from Alzheimer patients (AD+) spiked into plasma. The results were generated in the absence of (NT) or after treatment with streptomycin at various concentrations and analysis of the two pellet and supernatant fractions.

The results show that the phosphorylated Tau protein is found in the pellet after treatment with the agent I, streptomycin, at low concentration. Its presence in the sedimentation pellet attests to the fact that it has been concentrated by aggregation from the volume of sample tested, which is reflected by an increase in the detection compared with the analysis of the same sample in the absence of treatment with the agent I. These molecules therefore induce precipitation of the recombinant Tau protein after incubation for 60 minutes at 37° C. and simple centrifugation; the protein is then available for detection by means of an ELISA technique that can be used routinely in a clinical laboratory. However, it is seen that the precipitation is not complete since protein remains in the supernatant. Increasing the amount of agent I makes it possible to eliminate the presence of the protein in the supernatant for a concentration of 500 mg/ml. In this case, the precipitated protein is no longer detectable in the pellet by means of an ELISA technique. Analyses by Western blotting (data not provided) made it possible to verify that the protein is indeed present in aggregated form. In order to detect said aggregated form with an antibody, a suitable uptake buffer is necessary in order to reexpose the epitopes of each protein (see point 8.4).

8.4 Detection in the Presence of the Agent I, Streptomycin: Choice of Uptake Buffer The assays are carried out with 25 ng of brain extracts and with, as agent I, streptomycin, in sulfate form, at 500 mg/ml.

The samples are pretreated or not pretreated with SDS (1% final concentration).

Once the sample and the agent I have been brought into contact, in the presence or absence of SDS, the mixture is incubated for 60 minutes at 37° C.

The samples are then centrifuged for 10 minutes at 13 000 rpm. The pellets are recovered and are separated from the supernatants. All the fractions are conserved. The pellets are taken up with 250 µl of various solutions:

1% SDS 0.1M guanidine HCl (Gnd)

1M urea

1% SDS+0.1M guanidine HCl (Gnd)

1% SDS+1M urea 0.1M guanidine HCl (Gnd)+1M urea

1% SDS+0.1M guanidine HCl (Gnd)+1M urea.

The samples are then ready to be deposited onto plates.

The results (FIG. 14) show that, in the absence of SDS during the precipitation step, the detection of the protein is not optimal.

When the precipitation is carried out in the presence of SDS, the results differ according to the type of resuspension buffer used. Once again, the presence of SDS in this uptake buffer is essential. The best two combinations are SDS-guanidine and, better still, SDS-guanidine-urea, which allows a better intensity of detection. The Alzheimer-positive (PAD+) sample is then completely dissociated from the Alzheimer-negative (PAD−) sample or from the unspiked plasma (P). Its presence in the sedimentation pellet thus attests to the fact that it has been concentrated by aggregation from the volume of sample tested, which does not occur in the absence of agent I. These molecules therefore induce precipitation of the recombinant Tau protein after incubation for 60 minutes at 37° C. and simple centrifugation; the protein is then available for detection by means of an ELISA technique that can be used routinely in a clinical laboratory.

EXAMPLE 9

Detection of the Alpha-Synuclein Protein by Means of a Method Using a Precipitating Agent I 9.1 Analytical Technique: Protein Gel and Western Blotting The samples to be analyzed are denatured in an SDS buffer (125 mM Tris HCl, pH 6.8, 20% glycerol, 4% SDS, 0.02% bromophenol blue) (50/50 v/v) at 100° C. for 5 minutes. Said samples are then loaded onto a one-dimensional 12% polyacrylamide electrophoresis gel in the presence of sodium dodecyl sulfate (SDS-PAGE). After migration, two options are used:

- The protein gel is stained with Coomassie Blue by adding gelcode blue stain reagent (Pierce) overnight at ambient temperature with shaking. After washing in distilled water, the gel is incubated in drying solution (Pierce) for 15 minutes at ambient temperature with shaking and then dried between two sheets of cellophane at least overnight at ambient temperature.
- The analysis is carried out according to the Western blotting technique (Laemmli UK, 1970, Nature, 227: 680-685). The proteins are transferred onto a nitrocellulose membrane and immunoblotted at ambient temperature for one hour with an antibody specific for the protein Syn 211 (Zymed). The secondary detection antibody is a goat antibody (Jackson) which recognizes the heavy and light chains of mouse immunoglobulins G, conjugated to horseradish peroxidase. The membrane is washed, between each step, in phosphate buffered saline (PBS) with and then without Tween 20 (0.05% w/v). The signals are detected by chemiluminescence with the super signal kit (Pierce) and visualized on a radiographic film (Pierce).

9.2 Detection in the Presence of the Agent I

The assays are carried out with 1 μg of recombinant alpha-synuclein (SYN) protein (rPeptide) spiked into a pool of human plasmas and with, as agent I, either streptomycin, in sulfate form, or triethylenetetramine, or TET, at various concentrations.

Once the recombinant protein and the agent I have been brought into contact, the mixture is incubated for 60 minutes at 37° C.

The samples are then centrifuged for 10 minutes at 13 000 rpm. The pellets are recovered and are separated from the supernatants. All the fractions are conserved. The pellets are taken up with 250 μl of SDS buffer. After denaturation, all the fractions are analyzed by the Western blotting technique.

FIG. 15 gives the results obtained (schematic representation, top panel, and photo, bottom panel) on a protein gel after staining (FIG. 15A) and after Western blotting (FIG. 15B), obtained after migration of the SYN protein in the plasma after treatment with TET (lanes 2-5: pellets, 8-11: supernatants), lanes 1 and 7 correspond to the pellets and supernatants of the control sample without the addition of agent I, lane 6 contains molecular markers and lane 12 corresponds to the recombinant protein alone.

FIG. 16 gives the results obtained (schematic representation, top panel, and photo, bottom panel) on a protein gel after staining (FIG. 16A) and after Western blotting (FIG. 16B), obtained after migration of the SYN protein in the plasma after treatment with streptomycin (lanes 2-5: pellets, 8-11: supernatants), lanes 1 and 7 correspond to the pellets and supernatants of the control sample without the addition of agent I, lane 6 contains molecular weight markers and lane 12 corresponds to the recombinant protein alone.

The concentrations of agent I relative to the electrophoresis lanes are as indicated in Tables 7 and 8 below.

TABLE 7

(FIG. 15)

| Lane | Sample loaded | Fraction |
|---|---|---|
| 1 | Recombinant Syn in plasma | pellet |
| 2 | Recombinant Syn in plasma treated with 50 mg/ml TET | pellet |
| 3 | Recombinant Syn in plasma treated with 100 mg/ml TET | pellet |
| 4 | Recombinant Syn in plasma treated with 300 mg/ml TET | pellet |
| 5 | Recombinant Syn in plasma treated with 500 mg/ml TET | pellet |
| 6 | Molecular weight markers | NA |
| 7 | Recombinant Syn in plasma | supernatant |
| 8 | Recombinant Syn in plasma treated with 50 mg/ml TET | supernatant |
| 9 | Recombinant Syn in plasma treated with 100 mg/ml TET | supernatant |
| 10 | Recombinant Syn in plasma treated with 300 mg/ml TET | supernatant |
| 11 | Recombinant Syn in plasma treated with 500 mg/ml TET | supernatant |
| 12 | Nontreated recombinant Syn | no fractionation |

TABLE 8

(FIG. 16)

| Lane | Sample loaded | Fraction |
|---|---|---|
| 1 | Recombinant Syn in plasma | pellet |
| 2 | Recombinant Syn in plasma treated with 50 mg/ml streptomycin | pellet |
| 3 | Recombinant Syn in plasma treated with 100 mg/ml streptomycin | pellet |
| 4 | Recombinant Syn in plasma treated with 300 mg/ml streptomycin | pellet |
| 5 | Recombinant Syn in plasma treated with 500 mg/ml streptomycin | pellet |
| 6 | Molecular weight markers | NA |
| 7 | Recombinant Syn in plasma | supernatant |
| 8 | Recombinant Syn in plasma treated with 50 mg/ml streptomycin | supernatant |
| 9 | Recombinant Syn in plasma treated with 100 mg/ml streptomycin | supernatant |
| 10 | Recombinant Syn in plasma treated with 300 mg/ml streptomycin | supernatant |
| 11 | Recombinant Syn in plasma treated with 500 mg/ml streptomycin | supernatant |
| 12 | Nontreated recombinant Syn | no fractionation |

The results show that the Syn protein is found in the pellet after treatment with the agent I, irrespective of whether it is streptomycin or TET. Its presence in the sedimentation pellet attests to the fact that it has been concentrated by aggregation from the volume of sample tested. These molecules therefore induce precipitation of the recombinant Syn protein after incubation for 60 minutes at 37° C. and simple centrifugation. However, this precipitation is not complete since protein is found in the supernatant fraction. Nevertheless, this concentration is sufficient to allow its detection in an ELISA assay that can be used routinely in a clinical laboratory.

It will also be noted that this precipitation is relatively specific since the plasma proteins are predominantly found in the supernatant (FIGS. 15A and 16A, lanes 7-12)

EXAMPLE 10

Detection of the Alpha-Synuclein Protein by Means of a Method Using a Precipitating Agent II 10.1 Analytical Technique: Protein Gel and Western Blotting
The technique is the same as that described in Example 9.
10.2 Analytical technique: ELISA
The analysis is carried out according to the conventional "ELISA sandwich-type" immunoenzymatic technique: human alpha-synuclein ELISAkit (BioSource KHB0061) according to the supplier's recommendations.
10.3 Detection in the Presence of the Agent II
The assays are carried out with 1 μg recombinant alpha-synuclein (SYN) protein (rPeptide) spiked into a pool of human plasmas and with, as agent II, the calixarene p-sulfonato-3,7-(2-aminoethyloxy)-calix-[6]-arene (known as C6S). The assays are carried out as indicated in the previous example, except for the fact that C6S prepared as indicated in patent application WO2004/059322, with a concentration range of from 0 to 200 mg/ml, was used.

FIG. 17 gives the results obtained (schematic representation, top panel, and photo, bottom panel) on a protein gel, obtained after migration of the SYN protein in the plasma after treatment with the calixarenes. FIG. 17A corresponds to the pellet fraction, while FIG. 17B corresponds to the supernatants. Lanes 1 to 7 correspond to the Syn protein treated with various concentrations of calixarenes, lane 8 contains molecular weight markers and lane 9 corresponds to the nontreated recombinant protein.

The concentrations of agent II relative to the electrophoresis lanes are as indicated in Tables 9 and 10 below.

TABLE 9

(FIG. 17A)

| Lane | Sample loaded | Fraction |
|---|---|---|
| 1 | Recombinant Syn in plasma | pellet |
| 2 | Recombinant Syn in plasma treated with 2 mg/ml calixarene | pellet |
| 3 | Recombinant Syn in plasma treated with 5 mg/ml calixarene | pellet |
| 4 | Recombinant Syn in plasma treated with 10 mg/ml calixarene | pellet |
| 5 | Recombinant Syn in plasma treated with 50 mg/ml calixarene | pellet |
| 6 | Recombinant Syn in plasma treated with 100 mg/ml calixarene | pellet |
| 7 | Recombinant Syn in plasma treated with 200 mg/ml calixarene | pellet |
| 8 | Molecular weight markers | NA |
| 9 | Nontreated recombinant Syn | no fractionation |

TABLE 10

(FIG. 17B)

| Lane | Sample loaded | Fraction |
|---|---|---|
| 1 | Recombinant Syn in plasma | supernatant |
| 2 | Recombinant Syn in plasma treated with 2 mg/ml calixarene | supernatant |
| 3 | Recombinant Syn in plasma treated with 5 mg/ml calixarene | supernatant |
| 4 | Recombinant Syn in plasma treated with 10 mg/ml calixarene | supernatant |
| 5 | Recombinant Syn in plasma treated with 50 mg/ml calixarene | supernatant |
| 6 | Recombinant Syn in plasma treated with 100 mg/ml calixarene | supernatant |
| 7 | Recombinant Syn in plasma treated with 200 mg/ml calixarene | supernatant |
| 8 | Molecular weight markers | NA |
| 9 | Nontreated recombinant Syn | no fractionation |

The results show that, from a concentration of 10 mg/ml onward, the proteins of the plasma are exclusively found in the pellets (within the limit of sensitivity of the protein gel).

FIG. 18 gives the results obtained (schematic representation, top panel, and photo, bottom panel) from the autoradiography of an electrophoresis gel followed by Western blotting, obtained after migration of the SYN protein in the plasma after treatment with the calixarenes. FIG. 18A corresponds to the pellet fraction, while FIG. 18B corresponds to the supernatants. Lanes 1 to 7 correspond to the Syn protein treated with various concentrations of calixarenes, lane 8 contains molecular weight markers and lane 9 corresponds to the nontreated recombinant protein.

The concentrations of agent II relative to the electrophoresis lanes are as indicated in Tables 11 and 12 below.

TABLE 11

(FIG. 18A)

| Lane | Sample loaded | Fraction |
|---|---|---|
| 1 | Recombinant Syn in plasma | pellet |
| 2 | Recombinant Syn in plasma treated with 2 mg/ml calixarene | pellet |
| 3 | Recombinant Syn in plasma treated with 5 mg/ml calixarene | pellet |
| 4 | Recombinant Syn in plasma treated with 10 mg/ml calixarene | pellet |
| 5 | Recombinant Syn in plasma treated with 50 mg/ml calixarene | pellet |
| 6 | Recombinant Syn in plasma treated with 100 mg/ml calixarene | pellet |
| 7 | Recombinant Syn in plasma treated with 200 mg/ml calixarene | pellet |
| 8 | Molecular weight markers | NA |
| 9 | Nontreated recombinant Syn | no fractionation |

TABLE 12

(FIG. 18B)

| Lane | Sample loaded | Fraction |
|---|---|---|
| 1 | Recombinant Syn in plasma | supernatant |
| 2 | Recombinant Syn in plasma treated with 2 mg/ml calixarene | supernatant |
| 3 | Recombinant Syn in plasma treated with 5 mg/ml calixarene | supernatant |
| 4 | Recombinant Syn in plasma treated with 10 mg/ml calixarene | supernatant |
| 5 | Recombinant Syn in plasma treated with 50 mg/ml calixarene | supernatant |
| 6 | Recombinant Syn in plasma treated with 100 mg/ml calixarene | supernatant |
| 7 | Recombinant Syn in plasma treated with 200 mg/ml calixarene | supernatant |
| 8 | Molecular weight markers | NA |
| 9 | Nontreated recombinant Syn | no fractionation |

The results show that, the Syn protein is found in the pellet after treatment with the agent II. Its presence in the sedimentation pellet attests to the fact that it has been captured from the volume of sample tested. These molecules therefore induce capture of the recombinant Syn protein after incubation for 60 minutes at 37° C., but in this case, unexpectedly for an agent of type II, this capture makes it possible to precipitate the protein by simple centrifugation. However, this capture is not complete since protein is found in the supernatant fraction. The maximum amount of protein found in the pellet is done so for a calixarene concentration of between 10 and 50 mg/ml.

However, this concentrating is sufficient to allow its detection in an ELISA assay that can be used routinely in a clinical laboratory.

10.4 Sensitivity of Detection in the Presence of the Agent II

The assays are carried out with a range of recombinant alpha-synuclein (SYN) protein (rPeptide) spiked into a pool of human plasmas and with, as agent II, the calyxarene p-sulfonato-3,7-(2-aminoethyloxy)-calix-[6]-arene (known as C6S). The assays are carried out as indicated in the previous example, except for the fact that C6S prepared as indicated in patent application WO2004/059322 was used, with a concentration of 50 mg/ml.

FIG. 19 gives the results obtained (schematic representation, top panel, and photo, bottom panel) from the autoradiograph of an electrophoresis gel followed by Western blotting, obtained after migration of the SYN protein in the plasma after treatment with the calixarenes. FIG. 19A corresponds to the pellet fraction, while FIG. 19B corresponds to the supernatants. Lanes 1 to 8 correspond to various concentrations of the Syn protein treated with the calixarenes, lanes 10 to 12 correspond to the nontreated Syn protein and lane 9 contains molecular weight markers.

The concentrations of protein relative to the electrophoresis lanes are as indicated in Tables 13 and 14 below.

TABLE 13

(FIG. 19A)

| Lane | Sample loaded | Fraction |
|---|---|---|
| 1 | Recombinant Syn in plasma treated with calixarenes: 0 ng/ml | pellet |
| 2 | Recombinant Syn in plasma treated with calixarenes: 10 ng/ml | pellet |
| 3 | Recombinant Syn in plasma treated with calixarenes: 25 ng/ml | pellet |
| 4 | Recombinant Syn in plasma treated with calixarenes: 50 ng/ml | pellet |
| 5 | Recombinant Syn in plasma treated with calixarenes: 100 ng/ml | pellet |
| 6 | Recombinant Syn in plasma treated with calixarenes: 250 ng/ml | pellet |
| 7 | Recombinant Syn in plasma treated with calixarenes: 500 ng/ml | pellet |
| 8 | Recombinant Syn in plasma treated with calixarenes: 1000 ng/ml | pellet |
| 9 | Molecular weight markers | NA |
| 10 | Nontreated recombinant Syn in plasma: 0 ng/ml | no fractionation |
| 11 | Nontreated recombinant Syn in plasma: 10 ng/ml | no fractionation |
| 12 | Nontreated recombinant Syn in plasma: 25 ng/ml | no fractionation |

TABLE 14

(FIG. 19B)

| Lane | Sample loaded | Fraction |
|---|---|---|
| 1 | Recombinant Syn in plasma treated with calixarenes: 0 ng/ml | supernatant |
| 2 | Recombinant Syn in plasma treated with calixarenes: 10 ng/ml | supernatant |
| 3 | Recombinant Syn in plasma treated with calixarenes: 25 ng/ml | supernatant |
| 4 | Recombinant Syn in plasma treated with calixarenes: 50 ng/ml | supernatant |
| 5 | Recombinant Syn in plasma treated with calixarenes: 100 ng/ml | supernatant |
| 6 | Recombinant Syn in plasma treated with calixarenes: 250 ng/ml | supernatant |
| 7 | Recombinant Syn in plasma treated with calixarenes: 500 ng/ml | supernatant |
| 8 | Recombinant Syn in plasma treated with calixarenes: 1000 ng/ml | supernatant |
| 9 | Molecular weight markers | NA |
| 10 | Nontreated recombinant Syn in plasma: 50 ng/ml | no fractionation |
| 11 | Nontreated recombinant Syn in plasma: 100 ng/ml | no fractionation |
| 12 | Nontreated recombinant Syn in plasma: 250 ng/ml | no fractionation |

The results show that the Syn protein is found in the pellet after treatment with the agent II with a sensitivity of 25 ng/ml. Its presence in the sedimentation pellet attests to the fact that it has been captured, which in this case has created the conditions favorable to its precipitation from the volume of sample tested. These molecules therefore induce capture of the recombinant Syn protein after incubation for 60 minutes at 37° C. and promote its concentration by simple centrifugation. This capture is complete since the protein is not found in the supernatant fraction up to a concentration of 100 ng/ml. These results are confirmed by ELISA assay (see Example 10) (FIG. 20), where a concentration of 25 ng/ml is significantly detected in the pellet compared with the supernatant.

EXAMPLE 11

Detection of the Total Tau Protein in the Presence of an Agent II

Analytical Technique:

The analysis is carried out according to the conventional "ELISA sandwich-type" immunoenzymatic technique as described by Kohnken et al. (Neuroscience Letters 287 (2000) 187-190), with the calixarenes replacing the antibody normally used for capture.

The ELISA assay is based on the use of NHS-activated microplates onto which calixarenes are grafted at a concentration of 0.6 mg/ml for 2 h at ambient temperature. After having been washed 3 times in distilled water, the plates are vacuum-dried for 15 minutes at 37° C. The plates are then passivated with 200 μl/well of PBS containing 0.5% milk for 1 h at 37° C. After 3 washes in PBS containing 0.05% Tween20, the plates are ready for use.

Extracts of brains from patients suffering from (AD+) or not suffering from (AD−) Alzheimer's disease are diluted in a buffer containing 200 μg/ml of human albumin, 22 μg/ml of human IgG and 0.15 μg/ml of human IgM in a Krebs-Ringer bicarbonate buffer. Concentrations of 1 to 10 000 ng are tested; 100 μl of these dilutions are incubated for 1 h 30 at 37° C. 100 μl of a monoclonal mouse antibody specific for the Tau protein T14 (Zymed) at the concentration of 3 μg/ml diluted in PBS buffer containing 0.05% of Tween20 are then incubated for 1 h at 37° C.

In order to recognize the bound anti-Tau T14 antibody, a peroxidase-labeled goat anti-mouse IgG antibody (Jackson) is used at 0.5 µg/ml in PBS buffer containing 0.05% of Tween20 for 45 minutes at 37° C. A Lumiglo reagent (Kirkegaard and Perry laboratories, US) is added to each well and the chemiluminescence is read in a luminometer (Berthold, Centro LB 960). The data obtained are in the form of relative light units (RLU). Between each step described above, the wells are washed with PBS buffer containing 0.05% of Tween20.

The results in FIG. 21 show that the Tau protein is completely captured by the calixarenes up to a concentration of 1 ng/ml. This capture allows detection with a specific antibody in an ELISA assay format. Those skilled in the art will have noted a "hook effect" for the high concentrations of protein, a phenomenon which can be readily solved during optimization carried out by an expert. The differential obtained between the patients suffering from Alzheimer's disease (AD+) and the patients not suffering from Alzheimer's disease (AD−) allows this assay to be used routinely in a laboratory.

EXAMPLE 12

Detection of Syn Protein in the Presence of the Agents I and II

Analytical Technique

The first analysis is carried out according to the conventional "ELISA sandwich-type" immunoenzymatic technique: human alpha-synuclein ELISA kit (BioSource KHB0061) according to the supplier's recommendations.

The second analysis is carried out according to the conventional "ELISA sandwich-type" immunoenzymatic technique as described by Kohnken et al. (Neuroscience Letters 287 (2000) 187-190) with the calixarenes replacing the antibody normally used for capture.

The ELISA assay is based on the use of NHS-activated microplates onto which calixarenes (agent II) are grafted at a concentration of 0.6 mg/ml for two hours at ambient temperature. After having been washed 3 times in distilled water, the plates are vacuum-dried for 15 minutes at 37° C. The plates are then passivated with 200 µl/well of PBS containing 0.5% milk for 1 h at 37° C. After 3 washes in PBS containing 0.05% of Tween20, the plates are ready for use.

The assays are carried out with extracts of brains from patients suffering from Alzheimer's disease (20 µg/ml) and a recombinant alpha-synuclein (SYN) protein (rPeptide) (25 ng/ml), spiked into a pool of human plasmas.

The samples are precipitated in the presence of agent I (streptomycin at 500 mg/ml). Once the sample and the agent I have been brought into contact, the mixture is incubated for 60 minutes at 37° C.

The samples are then centrifuged for 10 minutes at 13 000 rpm. The pellets are recovered and are separated from the supernatants. All the fractions are conserved.

The pellets are taken up with 25 µl of 6M guanidine-HCl, possibly heated for 1 minute at 90° C., and then diluted in 225 µl of tris-maleate buffer. The samples are then ready to be deposited onto plates.

FIG. 22 shows the results obtained after precipitation with the agent I and detection with a conventional ELISA technique with antibody capture (first analysis; without the use of agent II). The results show that the recombinant protein is detected in the plasma after precipitation with the agent I; however, its precipitation in aggregated form does not allow optimal detection. The precipitation is also not complete, since the protein is detected in the supernatant and this monomeric form is completely captured by the antibodies. On the other hand, in the brain extract, where the protein is predominantly in aggregated form, it is immediately seen that the detection in the nontreated sample is weak and that, after treatment with an agent I, the protein is detected neither in the pellet nor in the supernatant under the operating conditions of this example.

FIG. 23 shows the results obtained after precipitation in aggregated form with the agent I and detection with a conventional ELISA technique with capture using the agent II. The results show that the recombinant protein and the brain extract are barely or not at all detected if they are not treated. On the other hand, after the action of the agent I, the advantage of using the agent II as capture tool can be very readily seen. Indeed, both in the case of the recombinant protein and in the case of the brain extract, the Syn protein in its aggregated form is completely detected in the precipitation pellet. Furthermore, the heating step makes it possible to improve the signal obtained.

It may therefore be concluded that the agent I/agent II combination makes it possible to improve the detection of the alpha-synuclein protein in a sample such as plasma.

EXAMPLE 13

Detection of the Phosphorylated Tau Protein in the Presence of the Agents I and II The analytical technique is the same as that described in Example 8, except that the capture antibodies are replaced with calixarenes (agent II) as described in Example 12. The detection antibody used is a monoclonal antibody developed by bioMérieux and used conjugated to peroxidase at a concentration of 1 µg/ml. This monoclonal antibody was obtained after immunization with a phosphorylated peptide derived from the Tau protein phosphorylated at position 231.

The sample used is an extract of brain from a patient suffering from Alzheimer's disease (AD pos) and spiked into a pool of plasma from normal patients. The assays are carried out with 25 ng of brain extract and with, as agent I, streptomycin, in sulfate form, at various concentrations.

Once the sample and the agent I have been brought into contact, the mixture is incubated for 60 minutes at 37° C. The samples are then centrifuged for 10 minutes at 13 000 rpm. The pellets are recovered and are separated from the supernatants. All the fractions are conserved. The pellets are taken up with 250 µl of tris-maleate buffer (unless otherwise indicated). The samples are then ready to be deposited onto plates.

The results in FIG. 24 show that the phosphorylated Tau protein is detected with difficulty in a nontreated plasma sample. On the other hand, it is clearly apparent that, after aggregation with the agent I, its detection in an ELISA assay, where the capture is carried out via an agent II, is made possible in the pellet. It may therefore be concluded that the agent I/agent II combination makes it possible to improve the detection of the phosphorylated Tau protein in a sample such as plasma.

The invention claimed is:

1. A method for detecting at least one aggregate-forming circulating protein form associated with noninfectious neurodegenerative diseases in a biological sample of human origin that may contain said aggregate-forming circulating protein forms, said aggregate-forming circulating protein forms containing:
   amino acids whose side chains have either an acid function or a hydrogen-bond-acceptor function being present overall at least four times in a peptide sequence of length less than or equal to twenty amino acids, and
   a minimum of three basic amino acids in a peptide sequence of a length of less than or equal to fifteen amino acids;
the method comprising:
   aggregating the circulating forms of the noninfectious proteins involved in pathological aggregation processes of the central nervous system by contacting the biological sample with a non-protein agent I selected from the group consisting of rifampicin, isoniazide ethambutol, triethylenetetraamine (TET), bis-3-aminopropylamine, spermine tetrahydrochloride, dihydrostreptomycin sesquisulfate, and streptomycin; and
   capturing natural aggregates of aggregate-forming circulating protein forms or the aggregates induced by said agent I by adding to the biological sample a non protein agent II selected from metacyclophane or a glycoaminoglycane; and
   revealing the presence of the aggregate-forming circulating protein forms.

2. The method for detecting at least one aggregate-forming circulating protein form as claimed in claim 1, wherein said agent I is added to said biological sample before said agent II is added to the biological sample.

3. The method for detecting at least one aggregate-forming circulating protein form as claimed in claim 1, further comprising at least one of the following additional steps i) and ii):
   i) separating the aggregates of aggregate-forming circulating protein forms from the reaction mixture, and
   ii) denaturing the aggregates of aggregate-forming circulating protein forms.

4. The method for detecting at least one aggregate-forming circulating protein form as claimed in claim 1, further comprising adding at least one binding partner specific for the aggregate-forming circulating protein forms for an immunoreaction between the binding partner specific for the aggregate-forming circulating protein forms and the aggregate-forming circulating protein forms.

5. The method for detecting at least one aggregate-forming circulating protein form as claimed in claim 1, wherein said agent II is bound to a solid support.

6. The method for detecting at least one aggregate-forming circulating protein form as claimed in claim 1, wherein said agent II corresponds to formula (I) below:

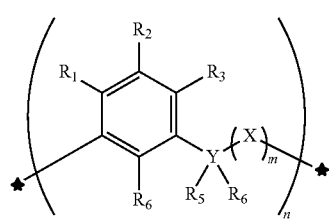

(I)

in which
   $R_1$ represents a hydrogen atom, a hydroxyl group, an OR group or an OCOR group, R being as defined below,
   $R_2$ represents a hydrogen atom, or an R, COR, Pol or $CH_2$Pol group, in which Pol represents a phosphate, sulfate, amine, ammonium or carboxylic acid group and R is as defined below,
   $R_3$ represents a hydrogen atom, a hydroxyl group, an OR group or an OCOR group in which R is as defined below,
   $R_4$ represents a hydrogen atom, a hydroxyl group, an OR group, an $OCH_2R$ group or an OCOR group, in which R is as defined below,
   Y is a carbon, nitrogen or sulfur atom,
   $R_5$ and $R_6$, each independently, are absent or represent a hydrogen atom, or a $CH_2$ or R group as defined below, or else
   $R_5$ and $R_6$ together represent an oxygen or sulfur atom,
   X represents a $CH_2$ group or an oxygen or sulfur atom,
   m represents an integer equal to 0 or 1,
   R represents a hydrogen atom or a branched or unbranched, cyclic or noncyclic, saturated or unsaturated hydrocarbon-based chain which is unsubstituted or substituted with a halogen group, and which bears polar or nonpolar functions,
   n is an integer between 3 and 15, and
   the substituents $R_1$ to $R_5$, R, X, Y and the integer m may be of different nature according to the units.

7. The method for detecting at least one aggregate-forming circulating protein form as claimed in claim 6, wherein said agent II corresponds to formula (Ia) below:

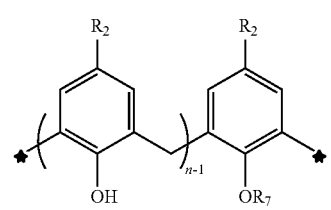

(Ia)

in which
   n is an integer between 4 and 8,
   each group $R_2$, taken independently, is a sulfate group or a phosphate group,
   $R_7$ represents a $(CH_2)_t$—$(CO)_s$—$(NH_2)$ group or a $(CH_2)_t$—COOH group where t is an integer between 0 and 6, and s is an integer between 0 and 6.

8. The method for detecting at least one aggregate-forming circulating protein form as claimed in claim 7, wherein said agent II is a calixarene of formula (Ia) in which the two groups $R_2$ are each a sulfate group, n is 4, 6 or 8, and $R_7$ is a hydrogen atom, a —$CH_2COOH$ group, a —$CH_2CONH_2$ group or a —$CH_2CH_2NH_2$ group.

9. The method for detecting aggregate-forming circulating protein forms as claimed in claim 8, wherein said agent II corresponds to formula (Ia) in which n=6, and $R_7$ is —$CH_2CH_2NH_2$.

10. The method for detecting at least one aggregate-forming circulating protein form as claimed in claim 1, wherein the metacyclophane is a calixarene.

11. The method for detecting at least one aggregate-forming circulating protein form as claimed in claim 1, wherein the metacyclophane is p-sulfonato-3,7-(2-aminoethyloxy)-calix-[6]-arene.

12. A method for detecting at least one aggregate-forming circulating protein form associated with noninfectious neurodegenerative diseases, said aggregate-forming circulating protein forms containing:
- amino acids whose side chains have either an acid function or a hydrogen-bond-acceptor function being present overall at least four times in a peptide sequence of length less than or equal to twenty amino acids, and
- a minimum of three basic amino acids in a peptide sequence of a length of less than or equal to fifteen amino acids;

the method comprising:
- bringing a biological sample, derived or obtained from a human organism, together with a non-protein agent I selected from the group consisting of rifampicin, isoniazide ethambutol, triethylenetetraamine (TET), bis-3-aminopropylamine, spermine tetrahydrochloride dihydrostreptomycin sesquisulfate and streptomycin to aggregate the circulating forms of the noninfectious proteins involved in pathological aggregation processes of the central nervous system; and
- revealing the presence of the aggregate-forming circulating protein forms.

13. The method for detecting at least one aggregate-forming circulating protein form as claimed in claim 12, wherein at least one binding partner specific for the aggregate-forming circulating protein forms is added for an immunoreaction between the binding partner specific for the aggregate-forming circulating protein forms and the aggregate-forming circulating protein forms.

14. A method for detecting at least one aggregate-forming circulating protein form associated with noninfectious neurodegenerative diseases, said aggregate-forming circulating protein form containing a minimum of three basic amino acids in a peptide sequence of a length of less than or equal to fifteen amino acids, the method comprising:
- bringing a biological sample, derived or obtained from a human organism, together with a non-protein agent II for capturing natural aggregates of aggregate-forming circulating protein forms, said agent II being a metacyclophane.

* * * * *